United States Patent [19]

McKay et al.

[11] Patent Number: 5,877,309
[45] Date of Patent: Mar. 2, 1999

[54] ANTISENSE OLIGONUCLEOTIDES AGAINST JNK

[75] Inventors: Robert McKay, La Mesa; Nicholas M. Dean, Encinitas, both of Calif.

[73] Assignee: ISIS Pharmaceuticals, Inc., Carlsbad, Calif.

[21] Appl. No.: 910,629

[22] Filed: Aug. 13, 1997

[51] Int. Cl.$^6$ .............. C07H 21/04; C12Q 1/68; C12N 15/85

[52] U.S. Cl. .......... 536/24.5; 435/6; 435/91.1; 435/172.1; 435/371; 435/375; 536/23.1; 536/24.3; 536/24.5

[58] Field of Search ............... 536/24.5, 24.3, 536/23.2, 23.1; 514/44; 435/320.1, 371, 16, 375, 91.1, 172.1

[56] References Cited

U.S. PATENT DOCUMENTS

| | | | |
|---|---|---|---|
| 4,309,404 | 1/1982 | Deneale et al. | 424/489 |
| 4,309,406 | 1/1982 | Guley et al. | 424/489 |
| 4,556,552 | 12/1985 | Porter et al. | 424/482 |
| 4,689,320 | 8/1987 | Kaji | 514/44 |
| 4,704,295 | 11/1987 | Porter et al. | 427/2.21 |
| 4,806,463 | 2/1989 | Goodchild et al. | 435/5 |
| 4,835,263 | 5/1989 | Nguyen et al. | 536/24.3 |
| 5,004,810 | 4/1991 | Draper | 536/24.5 |
| 5,034,506 | 7/1991 | Summerton et al. | 528/391 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,138,045 | 8/1992 | Cook et al. | 536/24.5 |
| 5,166,195 | 11/1992 | Ecker | 514/44 |
| 5,194,428 | 3/1993 | Agrawal et al. | 514/44 |
| 5,212,295 | 5/1993 | Cook | 536/26.7 |
| 5,218,105 | 6/1993 | Cook et al. | 536/25.31 |
| 5,223,618 | 6/1993 | Cook et al. | 544/276 |
| 5,242,906 | 9/1993 | Pagano et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,378,825 | 1/1995 | Cook et al. | 536/25.34 |
| 5,386,023 | 1/1995 | Sanghvi et al. | 536/25.3 |
| 5,457,191 | 10/1995 | Cook et al. | 536/27.13 |
| 5,459,255 | 10/1995 | Cook et al. | 536/27.13 |
| 5,506,351 | 4/1996 | McGee | 536/55.3 |
| 5,512,438 | 4/1996 | Ecker | 435/6 |
| 5,521,302 | 5/1996 | Cook | 536/25.31 |
| 5,539,082 | 7/1996 | Nielsen et al. | 530/300 |
| 5,541,307 | 7/1996 | Cook et al. | 536/23.1 |
| 5,554,746 | 9/1996 | Ravikumar et al. | 540/200 |
| 5,571,902 | 11/1996 | Ravikumar et al. | 536/22.1 |
| 5,578,718 | 11/1996 | Cook et al. | 536/27.21 |
| 5,587,361 | 12/1996 | Cook et al. | 514/44 |
| 5,587,469 | 12/1996 | Cook et al. | 536/23.1 |
| 5,587,470 | 12/1996 | Cook et al. | 536/23.1 |
| 5,599,797 | 2/1997 | Cook et al. | 514/44 |
| 5,602,240 | 2/1997 | De Mesmaeker et al. | 536/22.1 |
| 5,608,046 | 3/1997 | Cook et al. | 536/23.1 |
| 5,610,289 | 3/1997 | Cook et al. | 536/25.34 |

FOREIGN PATENT DOCUMENTS

| | | |
|---|---|---|
| WO 92/20823 | 11/1992 | WIPO. |
| WO 93/24510 | 12/1993 | WIPO. |
| WO 95/03324 | 2/1995 | WIPO. |
| WO 96/32496 | 10/1996 | WIPO. |
| WO 96/34008 | 10/1996 | WIPO. |

OTHER PUBLICATIONS

Ausubel et al., eds., "A Compendium of Methods from Current Protocols in Molecular Biology", Short Protocols in Molecular Biology, 2nd Ed., John Wiley & Sons, New York, 1992, pp. 3–11 to 3–44 and 4–17 to 4–18.

Ausubel et al., eds., "A Compendium of Methods from Current Protocols in Molecular Biology", Short Protocols in Molecular Biology, 2nd Ed., John Wiley & Sons, New York, 1992, pp. 2–24 to 2–30 and 4–14 to 4–29.

Ausubel et al., eds., "A Compendium of Methods from Current Protocols in Molecular Biology", Short Protocols in Molecular Biology, 2nd Ed., John Wiley & Sons, New York, 1992, pp. 10–33 to 10–35.

Alahari et al., The fission yeast prp4+ gene involved in pre–mRNA splicing codes for a predicted serine/threonine kinase and is essential for growth, Nucl. Acids Res., 1993, 21, 4079.

Albert et al., "Antisense knockouts: molecular scapels for the dissection of signal transduction", Trends Pharmacol. Sci., 1994, 15:250.

Angel et al., "Oncogene jun encodes a sequence–specific trans–activator similar to AP–1", Nature, 1988, 332, 166.

Angel and Karin, "The role of Jun, Fos and the AP–1 complex in cell–proliferation and transformation", Biochim. Biophys. Acta, 1991, 1072, 129.

Berge et al., "Pharmaceutical Salts," J. of Pharma Sci., 1977, 66:1.

Bernhard et al., "Direct evidence linking expression of matrix metalloproteinase 9 (92–kDa gelatinase/collagenase) to the metastatic phenotype in transformed rat embryo cells", Proc. Natl. Acad. Sci. U.S.A., 1994, 91, 4293.

Birkedal–Hansen, "Proteolytic remodeling of extracellular matrix", Current Op. Biol., 1995, 7, 728.

(List continued on next page.)

*Primary Examiner*—John L. LeGuyader
*Assistant Examiner*—Mark L. Shibuya
*Attorney, Agent, or Firm*—Law Offices of Jane Massey Licata

[57] ABSTRACT

Compositions and methods for the treatment and diagnosis of diseases or disorders amenable to treatment through modulation of expression of a gene encoding a Jun N-terminal kinase (JNK protein) are provided. Oligonucleotide are herein provided which are specifically hybridizable with nucleic acids encoding JNK1, JNK2 and JNK3, as well as other JNK proteins and specific isoforms thereof. Methods of treating animals suffering from diseases or disorders amenable to therapeutic intervention by modulating the expression of one or more JNK proteins with such oligonucleotide are also provided. Methods for the treatment and diagnosis of diseases or disorders associated with aberrant expression of one or more JNK proteins are also provided. The invention is thus directed to compositions for modulating, diagnostic methods for detecting, and therapeutic methods for inhibiting, the hyperproliferation of cells and formation, development and maintenance of tumors.

2 Claims, No Drawings

OTHER PUBLICATIONS

Binetruy et al., "Ha–Ras augments c–Jun activity and stimulates phosphorylation of its activation domain", Nature, 1991, 351, 122.

Blume and Cevc, "Liposomes for the sustained drug release in vivo", Biochem. et Biophys. Acta, 1990, 1029, 91.

Bohmann et al., "Human Proto–Oncogene c–jun Encodes a DNA Binding Protein with Structural and Functional Properties of Transcription Factor AP–1", Science, 1987, 238, 1386.

Brigstock et al., "Species–Specific High Molecular Weight Forms of Basic Fibroblast Growth Factor", Growth Factors, 1990, 4, 45.

Cano et al., "Parallel signal processing among mammalian MAPKs", Trends Biochem. Sci., 1995, 20, 117.

Chonn and Cullis, "Recent advances in liposomal drug–delivery systems", Current Op. Biotech., 1995, 6, 698.

Crooke et al., "Progress in the development and patenting of antisense drug discovery technology", Exp. Opin. Ther. Patents, 1996, 6:855.

Crooke et al., "Pharmacokinetic Properties of Several Novel Oligonucleotide Analogs in mice", J. Pharmacol. Exp. Ther., 1996, 277:923.

Crooke et al., eds., Chapter 26 In: Antisense Research and Applications, CRC Press, Boca Raton, FL, 1993, pp. 461–469.

Dean et al., "Inhibition of protein kinase C–a expression in mice after systemic administration of phosphorothioate antisense oligodeoxynucleotides", Proc. Natl. Acad. Sci. U.S.A., 1994, 91:11762–11766.

Derijard et al., "JNK1: A Protein Kinase Stimulated by UV Light and Ha–Ras That Binds and Phosphorylates the c–Jun Activation Domain", Cell, 1994, 76, 1025.

Fraley et al., Trends Biochem. Sci., 1981, 6, 77.

Ettinger et al., "Intrathecal Methotrexate Overdose Without Neurotoxicity", 1978, Cancer, 41, 1270, 1978.

Ewel et al., "Polyinosinic–Polycytidylic Acid Complexed with Poly–L–lysine and Carboxymethylcellulose in Combination with Interleukin 2 in Patients with Cancer: Clinical and Immunological Effects", Cancer Research, 1992, 52, 3005.

El–Hariri et al., "The Mitigating Effects of Phosphatidylcholines on Bile Salt– and Lysophosphatidylcholine–induced", J. Pharm. Pharmacol., 1992, 44:651.

Gao et al., "Cloning and Characterization of a Mouse Gene with Homology to the Human von Hippel–Lindau Disease Tumor Supressor Gene: Implications for the Potential Organization of the Human von Hippel–Lindau Disease Gene", Cancer Res., 1995, 55, 743.

Gelbert et al., "Analysis of GPT Activity in Mammalian Cells with a Chromosomally Integrated Shuttle Vector Containing Altered gpt Genes", Somat. Cell. Mol. Genet., 1990, 16, 173.

Gebeyehu, G., et al., "Novel biotinylated nucleotide — analogs for labeling and colorimetric detection of DNA", Nucleic Acids Res., 1987, 15, 4513.

Gold and Stormo, in: *Escherichia coli* and *Simonella typhimurium*: Cellular and Molecular Biology, vol. 2, 1987, Neidhardt et al., eds., "Transitional Initiation", American Society for Microbiology, Washington, D.C., pp. 1302–1307.

Gupta et al., "Selective interaction of JNK protein kinase isoforms with transcription factors", EMBO J., 1996, 15, 2760.

Gupta et al., "Transcription Factor ATF2 Regulation by the JNK Signal Transduction Pathway", Science, 1995, 267, 389.

Gum et al., "Stimulation of 92–kDa Gelatinase B Promoter Activity by ras Is Mitogen–activated Protein Kinase Kinase 1–independent and Requires Multiple Transcription Factor Binding Sites Including Closely Spaced PEA3/ets and AP–1 Sequences", J. Biol. Chem., 1996, 271, 10672.

Hibi et al., "Identification of an oncoprotein–and UV–responsive protein kinase that binds and potentiates the c–Jun activation domain", Genes & Dev., 1993, 7, 2135.

Himelstein et al., Invasion & Metastasis, 1994, 14, 246.

Harvey, "Absorption of Drugs", Chapter 35 In: Remington's Pharmaceutical Sciences, 18th Ed., Gennaro, ed. Mack Publishing Co., Easton, PA, 1990, p. 711.

Hirahata et al., Gan To Kagaku Ryoho, 1992, 19(10):1591.

Hua et al., "Inhibition of Matrix Metalloproteinase 9 Expression by a Ribozyme Blocks Metastasis ina Rat Sarcoma Model System $^2$", Cancer Res., 1996, 56, 5279.

Kabanov et al., "A new class of antivirals: antisense oligonucleotides combined with a hydrophobic substituent effectively inhibit influenza virus reproduction and synthesis of virus–specific proteins in MDCK cells", FEBS Lett., 1990, 259:327.

Kanagasundaram et al., "Isolation and characterization of the gene encoding gluconolactonase from *Zymomonas mobilis*", Biochim. Biophys. Acta, 1992, 1171, 198.

Kallunki et al., "JNK2 contains a specificity–determining region responsible for efficient c–Jun binding and phosphorylation", Genes & Development, 1994, 8, 2996.

Kemeny et al., "A Pilot Study of Hepatic Artery Floxuridine Combined with Systemic 5–Fluorouracil and Leucovorin", Cancer, 1993, 71, 1964.

Kerr et al., "Growth Factors Regulate Transin Gene Expression by c–fos–Dependent and c–fos–Independent Pathways", Science, 1988, 242, 1424–1427.

Kerr et al., "TGF–B1 Inhibition of Transin/Stromelysin Gene Expression Is Mediated through a Fos Binding Sequence", Cell, 1990,. 61, 267.

Kornberg, A., "Primary Structure$^{11}$", DNA Replication, W.H. Freeman & Co., San Francisco, 1980, pp. 4–7.

Kryiakis et al., "The stress–activated protein kinase subfamily of c–Jun kinases", Nature, 1994, 369, 156.

Letsinger et al., "Cholesteryl–conjugated oligonucleotides: Synthesis, properties, and activity as inhibitors of relication of human immunodeficiency virus in cell culture", Proc. Natl. Acad. Sci. U.S.A., 1989, 86:6553.

Lappalainen et al., "Cationic liposomes mediated delivery of antisense oligonucleotides targeted to HPV 16 E7 mRNA in CaSki cells", Antiviral Res., 1994, 23, 119.

Luer and Hatton, "Vancomycin Administration into the Cerebrospinal Fluid", The Annals of Pharmacotherapy, 1993, 27, 912.

Lee et al., "Critical Reviews in Therapeutic Drug Carrier Systems", Critical Reviews in Therapeutic Drug Carrier Systems, 1991, 8:91–192.

Martin et al., Helv. Chim. Acta, 1995, 78:486.

Morishita et al., "Single intraluminal delivery of antisense cdc2 kinase and proliferating–cell nuclear antigen oligonucleotides results in chronic inhibition of neointimal hyperplais", Proc. Natl. Acad. Sci. U.S.A, 1993, 90, 8474).

Mohit et al., "p49$^{3F12}$ Kinase: A Novel MAP Kinase Expressed in a Subset of Neurons in the Human Nervous System", Neuron, 1995, 14, 67.

Martin et al., "Developmental expression in the mouse nervous system of the p49$^{3F12}$ SAP kinase", Brain Res. Mol. Brain Res., 1996, 35, 47.

Manoharan et al., "Lipidic Nucleic Acids", Tetrahedron Lett., 1995, 36:3651.

Manoharan et al., "Oligonucleotide Conjugates: Alteration of the Pharmacokinetic Properties of Antisense Agents", Nucleosides & Nucleotides, 1995, 14:969.

Manoharan et al., "Cholic Acid–Oligonucleotide Conjugates for Antisense Applications", Bioorg. Med. Chem. Let., 1994, 4:1053.

Manoharan et al., "Antisense Strategies", Ann. N.Y. Acad. Sci., 1992, 660:307,309.

Manoharan et al., "Introduction of Lipophilic Thioether Tether in the minor gorrove of Nucleic acides for Antisense Applications", Bioorg. Med. Chem. Let., 1993, 3:2765.

Markussen et al., "Translational control of oskar generates Short OSK, the isoform that induces pole plasm assembly", Development, 1995, 121, 3723.

McDermott et al., "Structure and lens expression of the gene encoding chicken BA3/A1–crystallin", Gene, 1992, 117, 193.

The Merck Manual of Diagnosis and Therapy, "Ongology", 15th Ed., pp. 1206–1228, Berkow et al., eds., Rahay, N.J., 1987.

Monaco et al., "Structure of Two Rat Genes Coding for Closely Related Rolipram–sensitive cAMP Phosphodiesterases", J. Biol. Chem., 1994, 269, 347.

Mishra et al., "Improved leishmanicidal effect of phosphorotioate antisense oligonucleotides by LDL–mediated delivery", Biochim. Biophys. Acta, 1995, 1264:229.

Muranishi, "Absorption Enhancers", Critical Reviews in Therapeutic Drug Carrier Systems, 1990, 7:1.

Miyao et al., "Stability and Pharmacokinetic Characteristics of Oligonucleotides Modified at Terminal Linkages in Mice", Antisense Res. Dev., 1995, 5:115.

Mannino et al., "Liposome Mediated Gene Transfer", Biotechniques, 1988, 6, 682.

Nielsen et al., "Sequence–Selective Recognition of DNA by Strand Displacement with a Thymine–Substituted Polyamide", Science, 1991, 254:1497.

Oberhauser et al., "Effective incorporation of 2'–O–methyl–oligoribonucleotides into liposomes and enhanced cell association through modification with thiocholesterol", Nucl. Acids Res., 1992, 20:533.

Olsen et al., "Inhibition of Protein Kinase–A by Overexpression of the Cloned Human Protein Kinase Inhibitor", Mol. Endorcrinol., 1991, 5, 1246.

Perri et al., "Interactions of Plasmid–encoded Replication Initiation Proteins with the Origin of DNA Replication in the Broad Host Range Plasmid RK2*", J. Biol. Chem., 1991, 266, 12536.

Pushpa–Rekha et al., "Rat Phospholipid–hydroperoxide Glutathione Peroxidase", J. Biol. Chem., 1995, 270, 26993.

Raitano et al., "The Bcr–Abl leukemia oncogene activates Jun kinase and requires Jun for transformation", Proc. Natl. Acad. Sci. (USA), 1995, 92, 11746.

Rogers et al., "Alternative aplicing dictates tranlational start in Epstein–Barr virus transcipts", EMBO J., 1990, 9, 2373.

Rubenstein et al., "Antisense Oligonucleotide Intralesional Therapy for Human PC–3 Prostrate Tumors Carried in Athymic Nude Mice", J. Surg. Oncol., 1996, 62, 194.

Rudnic et al., "Oral Solid Dosage Forms", Chapter 89; In: Remington's Pharmaceutical Sciences, 18th Ed., Gennaro, ed., Mack Publishing Co., Easton, PA, 1990.

Ruth, "Oligonucleotide–Enzyme Conjugates", Chapter 6 In: Methods in Molecular Biology, vol. 26: Protocols for Oligonucleotide Conjugates Agrawal, ed., Humana Press Inc., Totowa, NJ, 1994, pp. 167–185.

Ruoslahti, "How Cancer Spreads", Sci. Amer., 1996, 275, 72.

Sambrook et al., eds., "Preparation of Radiolabeled DNA and RNA Probes", Chapter 10 In: Molecular Cloning: A Laboratory Manual, 2nd Ed., pp. 10.1–10.70.

Sambrook et al., eds., Extraction, Purification, and Analysis of Messenger RNA from Eukaryotic Cells, Chapter 7 In: Molecular Cloning: A Laboratory Manual, 2nd Ed., pp. 7.1–7.87.

Sambrook et al., "Labeling the 5 terminus of DNA with Bacteriophage T4 polynucleotide kinase", Molecular Cloning. A Laboratory Manual, Cold Spring Harbor Laboratory Press, 1989, vol. 2, p. 10.59.

Sluss et al., "Signal Transduction by Tumor Necrosis Factor Mediated by JNK Protein Kinases", Mol. Cel. Biol., 1994, 14, 8376.

Stetler–Stevenson et al., "Tumor Cell Interactions with the Extracellular Matrix During Invasion and Metastasis", Annu. Rev. Cell Biol., 1993, 9, 541.

Seger et al., "The MAPK signaling cascade", FASEB J., 1995, 9, 726.

Shaw, "Treatment of Intractable Cancer Pain by Elecgronically Controlled Parenteral Infusion of Analgesic Drugs", Cancer, 1993, 72(11), 3416.

Smeal et al., "Oncogenic and transcriptional cooperation with Ha–Ras requires phosphorylation of c–Jun on serines 63 and 73", Nature, 1991, 354, 494.

Saul et al., "celB, a Gene Coding for a Bifunctional Cellulase from the Extreme Thermophile 'Caldocellum saccharolyticum'", Appl. Environ. Microbiol., 1990, 56, 3117.

Saison–Behomaras et al., "Short modified antisense oligonucleotides directed against Ha–ras point mutation induce selective cleavage of the mRNA and inhibit T24 cells proliferation", EMBO J., 1991, 10:111.

Svinarchuk et al., "Inhibition of HIV proliferation in MT–4 cells by antisense oligonucleotide conjugated to lipophillic groups", Biochimie, 1993, 75:49.

Shea et al., "Synthesis, hybridization properties and antiviral activity of lipid–oligodeoxynucleotide conjugates", Nucl. Acids Res., 1990, 18:3777.

Takahashi et al., "The Use of a Perfluorochemical Emulsion as a Vascular Perfusate in Drug Absorption", J. Pharm. Pharmacol., 1988, 40:252.

Takakura et al., "Uptake Characteristics of Oligonucleotides in the Isolated Rat Liver Perfusion System", Antisense & Nucl. Acid Drug Dev., 1996, 6:177.

U.S. Congress, "The State–of–the–Art in Genetic Screening", Office of Technology Assessment, Chapter 5 In: Genetic Monitoring and Screening in the Workplace, OTA–BA–455, U.S. Government Printing Office, Washington, D.C., 1990, pp. 75–99.

Van Berge–Henegouwen et al., "Pharmacology of Chenodeoxycholic Acid", Gastroenterology, 1977, 73:300.

Whitesell et al., "Stability, clearance and disposition of intraventricularly administered oligodeoxynucleotides: Implications for therapeutic application within the central nervous system", Proc. Natl. Acad. Sci. (USA), 1993, 90, 4665.

Wahlestedt et al., "Modulation of Anxiety and Neuropeptide Y–Y1 Receptors by Antisense Oligodeoxynucleotides", Science, 1993, 259:528.

Wahlestedt et al., "Antisense oligodeoxynucleotides to NMDA–R1 receptor channel protect cortical neurons from excitotoxicity and reduce focal ischaemic infarctions", Nature, 1993, 363:260.

Yamashita et al., "Effects of diclofenac sodium and disodium ethylenediaminetetraacetate on electrical parameters of the mucosal membrane and their relation to their permeability enhancing effects inthe rat jejunum", J. Pharm. Pharmacol., 1987, 39:621.

Yaoita et al., "Xenopus laevis a and B thyroid hormone receptors", Proc. Natl. Acad. Sci. USA, 1990, 87, 7090.

Yaida et al., "Distribution of phosphodiester and phosphorothioate oligonucleotides in rat brain after intraventircular and intrahippocampal administration determined by in situ hybridization", Regul. Pept., 1995, 59, 193.

Zimm et al., "Cerebrospinal Fluid Pharmacokinetics of Intranventricular and Intravenous Aziridinylbenzoquinone", Cancer Research, 1984, 44, 1698.

Buur et al., J. Control Rel., 1990, 14:43.

Devirgilio et al., "Cloning and Disruption of a Gene Required for Growth on Acetate but not on Ethanol: the Acetyl–Coenzyme A Synthetase Gene of *Saccharomyces cerevisiae*", Yeast, 1992, 8, 1043.

Merriam Webster's Collegiate Dictionary, Tenth Edition, Merriam Webster, Inc. (1996). p. 250.

Rojanasakul, Antisense Oligonucleotide Therapeutics: Drug Delivery and Targeting, Advanced Drug Delivery Reviews, V. 18, 115–131 (1996). p. 118.

Seimiya et al., C–Jun NH2–Terminal Kinase–Mediated Activation of Interleukin–1Beta Converting Enzyme/CED–3–like Protease During Anticancer Drug–Induced Apoptosis, J. Biol. Chem. V. 272(7), 4631–4636 (Feb. 20, 1997).

Derijard et al., JNK1: A Protein Kinase Stimulated by UV Light and Ha–Ras that Binds and Phosphorylates the c–Jun Activation Domain, Cell V. 76, 1025–1037, (Apr. 6, 1994).

Milligan et al., Current Concepts in Antisense Drug Design, J Medicinal Chem. V. 36(14) 1923–1937 (1993).

Kallunki et al., JNK2 Contains a Specificity–Determining Region Responsible for Efficient c–Jun Binding and Phosphorylation, Genes & Devel. V. 8, 2996–3007 (1994).

Shibahara et al., Inhibition of Human Immunodeficiency Virus (HIV–1) Replication by Synthetic Oligo–RNA Derivatives, Nucleic Acids Res. V. 17 (1), 239–252 (1989).

SEQUENCE LISTING ( 1 ) GENERAL INFORMATION:

( i i i ) NUMBER OF SEQUENCES: 86

( 2 ) INFORMATION FOR SEQ ID NO: 1:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 1:

ATTCTTTCCA CTCTTCTATT        20

( 2 ) INFORMATION FOR SEQ ID NO: 2:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 2:

CTCCTCCAAG TCCATAACTT        20

( 2 ) INFORMATION FOR SEQ ID NO: 3:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 3:

CCCGTATAAC TCCATTCTTG                    20

( 2 ) INFORMATION FOR SEQ ID NO: 4:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 4:

CTGTGCTAAA GGAGAGGGCT                    20

( 2 ) INFORMATION FOR SEQ ID NO: 5:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 5:

ATGATGGATG CTGAGAGCCA                    20

( 2 ) INFORMATION FOR SEQ ID NO: 6:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 6:

GTTGACATTG AAGACACATC                    20

( 2 ) INFORMATION FOR SEQ ID NO: 7:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 7:

CTGTATCAGA GGCCAAAGTC                    20

( 2 ) INFORMATION FOR SEQ ID NO: 8:

( i ) SEQUENCE CHARACTERISTICS:
        ( A ) LENGTH: 20
        ( B ) TYPE: Nucleic Acid
        ( C ) STRANDEDNESS: Single (D) TOPOLOGY: Linear (iv) ANTI-SENSE: Yes (xi) SEQUENCE DESCRIPTION: SEQ ID NO: 8:

TGCTGCTTCT AGACTGCTGT                                            20

(2) INFORMATION FOR SEQ ID NO: 9:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 9:

AGTCATCTAC AGCAGCCCAG                                            20

(2) INFORMATION FOR SEQ ID NO: 10:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 10:

CCATCCCTCC CACCCCCCGA                                            20

(2) INFORMATION FOR SEQ ID NO: 11:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 11:

ATCAATGACT AACCGACTCC                                            20

(2) INFORMATION FOR SEQ ID NO: 12:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 12:

CAAAAATAAG ACCACTGAAT                                            20

(2) INFORMATION FOR SEQ ID NO: 13:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 13:

CACGCTTGCT TCTGCTCATG 20

( 2 ) INFORMATION FOR SEQ ID NO: 14:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 14:

CGGCTTAGCT TCTTGATTGC 20

( 2 ) INFORMATION FOR SEQ ID NO: 15:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 15:

CCCGCTTGGC ATGAGTCTGA 20

( 2 ) INFORMATION FOR SEQ ID NO: 16:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 16:

CTCTCTGTAG GCCCGCTTGG 20

( 2 ) INFORMATION FOR SEQ ID NO: 17:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 17:

ATTTGCATCC ATGAGCTCCA 20

( 2 ) INFORMATION FOR SEQ ID NO: 18:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 18:

CGTTCCTGCA GTCCTGGCCA 20

( 2 ) INFORMATION FOR SEQ ID NO: 19:

( i ) SEQUENCE CHARACTERISTICS:
  ( A ) LENGTH: 20
  ( B ) TYPE: Nucleic Acid
  ( C ) STRANDEDNESS: Single
  ( D ) TOPOLOGY: Linear ( i v ) ANTI-SENSE: Yes ( x i ) SEQUENCE DESCRIPTION: SEQ ID NO: 19:

GGATGACCTC GGGTGCTCTG      20

( 2 ) INFORMATION FOR SEQ ID NO: 20:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 20:

CCCATAATGC ACCCCACAGA      20

( 2 ) INFORMATION FOR SEQ ID NO: 21:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 21:

CGGGTGTTGG AGAGCTTCAT      20

( 2 ) INFORMATION FOR SEQ ID NO: 22:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 22:

TTTGGTGGTG GAGCTTCTGC      20

( 2 ) INFORMATION FOR SEQ ID NO: 23:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 23:

GGCTGCCCCC GTATAACTCC      20

( 2 ) INFORMATION FOR SEQ ID NO: 24:

( i ) SEQUENCE CHARACTERISTICS:
    ( A ) LENGTH: 20
    ( B ) TYPE: Nucleic Acid
    ( C ) STRANDEDNESS: Single (D) TOPOLOGY: Linear (iv) ANTI-SENSE: Yes (xi) SEQUENCE DESCRIPTION: SEQ ID NO: 24:

TGCTAAAGGA GAGGGCTGCC        20

(2) INFORMATION FOR SEQ ID NO: 25:

(i) SEQUENCE CHARACTERISTICS:
      (A) LENGTH: 20
      (B) TYPE: Nucleic Acid
      (C) STRANDEDNESS: Single
      (D) TOPOLOGY: Linear (iv) ANTI-SENSE: Yes (xi) SEQUENCE DESCRIPTION: SEQ ID NO: 25:

AGGCCAAAGT CGGATCTGTT        20

(2) INFORMATION FOR SEQ ID NO: 26:

(i) SEQUENCE CHARACTERISTICS:
      (A) LENGTH: 20
      (B) TYPE: Nucleic Acid
      (C) STRANDEDNESS: Single
      (D) TOPOLOGY: Linear (iv) ANTI-SENSE: Yes (xi) SEQUENCE DESCRIPTION: SEQ ID NO: 26:

CCACCCCCG ATGGCCAAG        20

(2) INFORMATION FOR SEQ ID NO: 27:

(i) SEQUENCE CHARACTERISTICS:
      (A) LENGTH: 20
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 27:

CCAAGCGGGC CTACAGAGAG        20

(2) INFORMATION FOR SEQ ID NO: 28:

(i) SEQUENCE CHARACTERISTICS:
      (A) LENGTH: 20
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 28:

CTTTCCGTTG GACCCCTGGG        20

(2) INFORMATION FOR SEQ ID NO: 29:

(i) SEQUENCE CHARACTERISTICS:
      (A) LENGTH: 20
      (B) TYPE: Nucleic Acid
      (C) STRANDEDNESS: Single
      (D) TOPOLOGY: Linear (iv) ANTI-SENSE: Yes (xi) SEQUENCE DESCRIPTION: SEQ ID NO: 29:

GTTTCAGATC CCTCGCCCGC 20

( 2 ) INFORMATION FOR SEQ ID NO: 30:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 30:

TGCAGCACAA ACAATCCCTT 20

( 2 ) INFORMATION FOR SEQ ID NO: 31:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 31:

GTCCGGGCCA GGCCAAAGTC 20

( 2 ) INFORMATION FOR SEQ ID NO: 32:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 32:

CAGGATGACT TCGGGCGCCC 20

( 2 ) INFORMATION FOR SEQ ID NO: 33:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 33:

GCTCTCCCAT GATGCAACCC 20

( 2 ) INFORMATION FOR SEQ ID NO: 34:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 34:

ATGGGTGACG CAGAGCTTCG 20

( 2 ) INFORMATION FOR SEQ ID NO: 35:

( i ) SEQUENCE CHARACTERISTICS:
  ( A ) LENGTH: 20
  ( B ) TYPE: Nucleic Acid
  ( C ) STRANDEDNESS: Single
  ( D ) TOPOLOGY: Linear ( i v ) ANTI-SENSE: Yes ( x i ) SEQUENCE DESCRIPTION: SEQ ID NO: 35:

CTGCTGCATC TGAAGGCTGA 20

( 2 ) INFORMATION FOR SEQ ID NO: 36:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 36:

TGAGAAGGAG TGGCGTTGCT 20

( 2 ) INFORMATION FOR SEQ ID NO: 37:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 37:

TGCTGTCTGT GTCTGAGGCC 20

( 2 ) INFORMATION FOR SEQ ID NO: 38:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 38:

GGTCCCGTCG AGGCATCAAG 20

( 2 ) INFORMATION FOR SEQ ID NO: 39:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 39:

CATTTCAGGC CCACGGAGGT 20

( 2 ) INFORMATION FOR SEQ ID NO: 40:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear (i v) ANTI-SENSE: Yes (x i) SEQUENCE DESCRIPTION: SEQ ID NO: 40:

GGTCTGAATA GGGCAAGGCA 20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 41:

GGGCAAGTCC AAGCAAGCAT 20

(2) INFORMATION FOR SEQ ID NO: 42:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: No (x i) SEQUENCE DESCRIPTION: SEQ ID NO: 42:

GACTTTGGCC TGGCCCGGAC 20

(2) INFORMATION FOR SEQ ID NO: 43:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: No (x i) SEQUENCE DESCRIPTION: SEQ ID NO: 43:

GTGCGCGCGA GCCCGAAATC 20

(2) INFORMATION FOR SEQ ID NO: 44:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 44:

TTCAACAGTT TCTTGCATAA 20

(2) INFORMATION FOR SEQ ID NO: 45:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 45:

CTCATCTATA GGAAACGGGT 20

( 2 ) INFORMATION FOR SEQ ID NO: 46:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 46:

TGGAGGCTCA TAAATACCAC　　　　　　　　　　　　　　　　　　20

( 2 ) INFORMATION FOR SEQ ID NO: 47:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 47:

TATAAGAAAT GGAGGCTCAT　　　　　　　　　　　　　　　　　　20

( 2 ) INFORMATION FOR SEQ ID NO: 48:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 48:

TCACATCCAA TGTTGGTTCA　　　　　　　　　　　　　　　　　　20

( 2 ) INFORMATION FOR SEQ ID NO: 49:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 49:

TTATCGAATC CCTGACAAAA　　　　　　　　　　　　　　　　　　20

( 2 ) INFORMATION FOR SEQ ID NO: 50:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 50:

GTTTGGCAAT ATATGACACA　　　　　　　　　　　　　　　　　　20

( 2 ) INFORMATION FOR SEQ ID NO: 51:

( i ) SEQUENCE CHARACTERISTICS:

(A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 51:

CTGTCAAGGA CAGCATCATA 20

(2) INFORMATION FOR SEQ ID NO: 52:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 52:

AATCACTTGA CATAAGTTGG 20

(2) INFORMATION FOR SEQ ID NO: 53:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 53:

TAAATCCCTG TGAATAATTC 20

(2) INFORMATION FOR SEQ ID NO: 54:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 54:

GCATCCCACA GACCATATAT 20

(2) INFORMATION FOR SEQ ID NO: 55:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 55:

TGTTCTCTTT CATCCAACTG 20

(2) INFORMATION FOR SEQ ID NO: 56:

(i) SEQUENCE CHARACTERISTICS:
            (A) LENGTH: 20
            (B) TYPE: Nucleic Acid
            (C) STRANDEDNESS: Single
            (D) TOPOLOGY: Linear (i v) ANTI-SENSE: Yes (x i) SEQUENCE DESCRIPTION: SEQ ID NO: 56:

TCTCACTGCT GTTCACTGCT 20

(2) INFORMATION FOR SEQ ID NO: 57:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 57:

GGGTCTGGTC GGTGGACATG 20

(2) INFORMATION FOR SEQ ID NO: 58:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 58:

AGGCTGCTGT CAGTGTCAGA 20

(2) INFORMATION FOR SEQ ID NO: 59:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 59:

TCACCTGCAA CAACCCAGGG 20

(2) INFORMATION FOR SEQ ID NO: 60:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 60:

GCGGCTAGTC ACCTGCAACA 20

(2) INFORMATION FOR SEQ ID NO: 61:

(i) SEQUENCE CHARACTERISTICS:
        (A) LENGTH: 20
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 61:

CGCTGGGTTT CGCAGGCAGG 20

( 2 ) INFORMATION FOR SEQ ID NO: 62:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 62:

ATCATCTCCT GAAGAACGCT                                            20

( 2 ) INFORMATION FOR SEQ ID NO: 63:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 63:
                AACGTGGATT TATGGTCTGT GGGGTGCATT ATGGG    35

( 2 ) INFORMATION FOR SEQ ID NO: 64:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 64:

AACGTTGACA TTTGGTCAGT TGGGTGCATC ATGGG                              35

( 2 ) INFORMATION FOR SEQ ID NO: 65:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 65:

CCCATAATGC ACCCCACAGA CCATAAATCC ACGTT                              35

( 2 ) INFORMATION FOR SEQ ID NO: 66:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 66:

CCCATGATGC ACCCAACTGA CCAAATGTCA ACGTT                              35

( 2 ) INFORMATION FOR SEQ ID NO: 67:

( i ) SEQUENCE CHARACTERISTICS:
        ( A ) LENGTH: 44
        ( B ) TYPE: Nucleic Acid ( C ) STRANDEDNESS: Single
            ( D ) TOPOLOGY: Linear ( i v ) ANTI-SENSE: No ( x i ) SEQUENCE DESCRIPTION: SEQ ID NO: 67:

AAATGGTTTG CCACAAAATC CTCTTTCCAG GAAGGGACTA TATT 44

( 2 ) INFORMATION FOR SEQ ID NO: 68:

( i ) SEQUENCE CHARACTERISTICS:
            ( A ) LENGTH: 44
            ( B ) TYPE: Nucleic Acid
            ( C ) STRANDEDNESS: Single
            ( D ) TOPOLOGY: Linear ( i v ) ANTI-SENSE: No ( x i ) SEQUENCE DESCRIPTION: SEQ ID NO: 68:

AAATGATCAA AGGTGGTGTT TTGTTCCCAG GTACAGATCA TATT 44

( 2 ) INFORMATION FOR SEQ ID NO: 69:

( i ) SEQUENCE CHARACTERISTICS:
            ( A ) LENGTH: 44
            ( B ) TYPE: Nucleic Acid
            ( C ) STRANDEDNESS: Single
            ( D ) TOPOLOGY: Linear ( i v ) ANTI-SENSE: Yes ( x i ) SEQUENCE DESCRIPTION: SEQ ID NO: 69:

AATATAGTCC CTTCCTGGAA AGAGGATTTT GTGGCAAACC ATTT 44

( 2 ) INFORMATION FOR SEQ ID NO: 70:

( i ) SEQUENCE CHARACTERISTICS:
            ( A ) LENGTH: 44
            ( B ) TYPE: Nucleic Acid
            ( C ) STRANDEDNESS: Single
            ( D ) TOPOLOGY: Linear ( i v ) ANTI-SENSE: Yes ( x i ) SEQUENCE DESCRIPTION: SEQ ID NO: 70:

AATATGATCT GTACCTGGGA ACAAAACACC ACCTTTGATC 40

ATTT 44

( 2 ) INFORMATION FOR SEQ ID NO: 71:

( i ) SEQUENCE CHARACTERISTICS:
            ( A ) LENGTH: 32
            ( B ) TYPE: Nucleic Acid
            ( C ) STRANDEDNESS: Single
            ( D ) TOPOLOGY: Linear ( i v ) ANTI-SENSE: No ( x i ) SEQUENCE DESCRIPTION: SEQ ID NO: 71:

CCCTCTCCTT TAGCACAGGT GCAGCAGTGA TC 32

( 2 ) INFORMATION FOR SEQ ID NO: 72:

( i ) SEQUENCE CHARACTERISTICS:
            ( A ) LENGTH: 27
            ( B ) TYPE: Nucleic Acid
            ( C ) STRANDEDNESS: Single
            ( D ) TOPOLOGY: Linear (i v) ANTI-SENSE: No (x i) SEQUENCE DESCRIPTION: SEQ ID NO: 72:

CCCTCTCCTT TAGGTGCAGC AGTGATC                                                                 27

(2) INFORMATION FOR SEQ ID NO: 73:

(i) SEQUENCE CHARACTERISTICS:
        (A) LENGTH: 32
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 73:

GATCACTGCT GCACCTGTGC TAAAGGAGAG GG                                                           32

(2) INFORMATION FOR SEQ ID NO: 74:

(i) SEQUENCE CHARACTERISTICS:
        (A) LENGTH: 27
        (B) TYPE: Nucleic Acid
        (C) STRANDEDNESS: Single
        (D) TOPOLOGY: Linear (i v) ANTI-SENSE: Yes (x i) SEQUENCE DESCRIPTION: SEQ ID NO: 74:

GATCACTGCT GCACCTAAAG GAGAGGG                                                                 27

(2) INFORMATION FOR SEQ ID NO: 75:

(i) SEQUENCE CHARACTERISTICS:
        (A) LENGTH: 60
        (B) TYPE: Nucleic Acid
        (C) STRANDEDNESS: Single
        (D) TOPOLOGY: Linear (i v) ANTI-SENSE: No (x i) SEQUENCE DESCRIPTION: SEQ ID NO: 75:

GTGGGTTGCA TCATGGGAGA GCTGGTGAAA GGTTGTGTGA TATTCCAAGG                                        50

CACTGACCAT                                                                                    60

(2) INFORMATION FOR SEQ ID NO: 76:

(i) SEQUENCE CHARACTERISTICS:
        (A) LENGTH: 60
        (B) TYPE: Nucleic Acid
        (C) STRANDEDNESS: Single
        (D) TOPOLOGY: Linear (i v) ANTI-SENSE: No (x i) SEQUENCE DESCRIPTION: SEQ ID NO: 76:

GTCGGGTGCA TCATGGCAGA AATGGTCCTC CATAAAGTCC TGTTCCCGGG                                        50

AAGAGACTAT                                                                                    60

(2) INFORMATION FOR SEQ ID NO: 77:

(i) SEQUENCE CHARACTERISTICS:
        (A) LENGTH: 60
        (B) TYPE: Nucleic Acid
        (C) STRANDEDNESS: Single
        (D) TOPOLOGY: Linear (i v) ANTI-SENSE: Yes ( x i ) SEQUENCE DESCRIPTION: SEQ ID NO: 77:

ATGGTCAGTG CCTTGGAATA TCACACAACC TTTCACCAGC TCTCCATGA 50

TGCAACCCAC 60

( 2 ) INFORMATION FOR SEQ ID NO: 78:

( i ) SEQUENCE CHARACTERISTICS:
        ( A ) LENGTH: 60
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 78:

ATAGTCTCTT CCCGGGAACA GGACTTTATG GAGGACCATT TCTGCCATGA 50

TGCACCCGAC 60

( 2 ) INFORMATION FOR SEQ ID NO: 79:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 79:

GATCAGCCTT CAGCACAGAT GCAGCAGTAA GTAGC 35

( 2 ) INFORMATION FOR SEQ ID NO: 80:

( i ) SEQUENCE CHARACTERISTICS:
        ( A ) LENGTH: 30
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 80:

GATCAGCCTT CAGATGCAGC AGTAAGTAGC 30

( 2 ) INFORMATION FOR SEQ ID NO: 81:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 81:

GCTACTTACT GCTGCATCTG TGCTGAAGGC TGATC 35

( 2 ) INFORMATION FOR SEQ ID NO: 82:

( i ) SEQUENCE CHARACTERISTICS:
        ( A ) LENGTH: 30
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 82:

```
GCTACTTACT  GCTGCATCTG  AAGGCTGATC                                                30
```

( 2 ) INFORMATION FOR SEQ ID NO: 83:

( i ) SEQUENCE CHARACTERISTICS:
        ( A ) LENGTH: 38
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 83:

```
GGACAGCCTT  CTCCTTCAGC  ACAGGTGCAG  CAGTGAAC                          38
```

( 2 ) INFORMATION FOR SEQ ID NO: 84:

( i ) SEQUENCE CHARACTERISTICS:
        ( A ) LENGTH: 33
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 84:

```
GGACAGCCTT  CTCCTTCAGG  TGCAGCAGTG  AAC                               33
```

( 2 ) INFORMATION FOR SEQ ID NO: 85:

( i ) SEQUENCE CHARACTERISTICS:
        ( A ) LENGTH: 38
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 85:

```
GTTCACTGCT  GCACCTGTGC  TGAAGGAGAA  GGCTGTCC                          38
```

( 2 ) INFORMATION FOR SEQ ID NO: 86:

( i ) SEQUENCE CHARACTERISTICS:
        ( A ) LENGTH: 33
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 86:

```
GTTCACTGCT  GCACCTGAAG  GAGAAGGCTG  TCC                               33
```

ANTISENSE OLIGONUCLEOTIDES AGAINST JNK

FIELD OF THE INVENTION

The present invention provides compositions and methods for detecting and modulating levels of Jun N-terminal kinases (JNK proteins), enzymes which are encoded by JNK genes. In particular, the invention relates to antisense oligonucleotides specifically hybridizable with nucleic acids encoding JNK proteins. It has been found that antisense oligonucleotides can modulate the expression of these and other JNK proteins, kinases which were initially discovered due to their ability to catalyze the phosphorylation of the c-Jun subunit of transcription factor AP-1 and thereby increase AP-1 activity. Other transcription factors, such as ATF-2, are similarly activated by JNK proteins, and a variety of other cellular effectors may serve as substrates for JNK proteins (Gupta et al., *Science,* 1995, 267, 389). In any event, transcription factor AP-1 has been implicated in abnormal cell proliferation, oncogenic transformation, and tumor formation, development and maintenance (Vogt, Chapter 15 In: The FOS and JUN *Families of Transcription Factors,* Angel and Herrlich, Eds., CRC Press, Boca Raton, Fla., 1994). Accordingly, it is believed that (1) JNK proteins are aberrantly expressed in some neoplasms and tumors with resultant increased AP-1 activity, and (2) even in abnormally proliferating cells in which a JNK gene is not aberrantly expressed, inhibition of JNK expression will result in decreased AP-1 activity and thus, inhibition of abnormal cell proliferation and tumor formation, development and maintenance. The invention is thus directed to diagnostic methods for detecting, and therapeutic methods for inhibiting, the hyperproliferation of cells and the formation, development and maintenance of tumors. Furthermore, this invention is directed to treatment of conditions associated with abnormal expression of JNK genes. This invention also relates to therapies, diagnostics, and research reagents for disease states or disorders which respond to modulation of the expression of JNK proteins. Inhibition of the hyperproliferation of cells, and corresponding prophylactic, palliative and therapeutic effects result from treatment with the oligonucleotides of the invention.

BACKGROUND OF THE INVENTION

Transcription factors play a central role in the expression of specific genes upon stimulation by extracellular signals, thereby regulating a complex array of biological processes. Members of the family of transcription factors termed AP-1 (activating protein-1) alter gene expression in response to growth factors, cytokines, tumor promoters, carcinogens and increased expression of certain oncogenes (Rahmsdorf, Chapter 13, and Rapp et al., Chapter 16 In: The FOS and JUN *Families of Transcription Factors,* Angel and Herrlich, Eds., CRC Press, Boca Raton, Fla., 1994). Growth factors and cytokines exert their function by binding to specific cell surface receptors. Receptor occupancy triggers a signal transduction cascade to the nucleus. In this cascade, transcription factors such as AP-1 execute long term responses to the extracellular factors by modulating gene expression. Such changes in cellular gene expression lead to DNA synthesis, and eventually the formation of differentiated derivatives (Angel and Karin, *Biochim. Biophys. Acta,* 1991, 1072, 129).

In general terms, AP-1 denotes one member of a family of related heterodimeric transcription factor complexes found in eukaryotic cells or viruses (The FOS and JUN *Families of Transcription Factors,* Angel and Herrlich, Eds., CRC Press, Boca Raton, Fla. 1994; Bohmann et al., *Science,* 1987, 238, 1386; Angel et al., *Nature,* 1988, 332, 166). Two relatively well-characterized AP-1 subunits are c-Fos and c-Jun; these two proteins are products of the c-fos and c-jun proto-oncogenes, respectively. Repression of the activity of either c-fos or c-jun, or of both proto-oncogenes, and the resultant inhibition of the formation of c-Fos and c-Jun proteins, is desirable for the inhibition of cell proliferation, tumor formation and tumor growth.

The phosphorylation of proteins plays a key role in the transduction of extracellular signals into the cell. Mitogen-activated protein kinases (MAPKs), enzymes which effect such phosphorylations are targets for the action of growth factors, hormones, and other agents involved in cellular metabolism, proliferation and differentiation (Cobb et al., *J. Biol. Chem.,* 1995, 270, 14843). MAPKs (also referred to as extracellular signal-regulated protein kinases, or ERKs) are themselves activated by phosphorylation catalyzed by, e.g., receptor tyrosine kinases, G protein-coupled receptors, protein kinase C (PKC), and the apparently MAPK-dedicated kinases MEK1 and MEK2. In general, MAP kinases are involved in a variety of signal transduction pathways (sometimes overlapping and sometimes parallel) that function to convey extracellular stimuli to proto-oncogene products to modulate cellular proliferation and/or differentiation (Seger et al., *FASEB J.,* 1995, 9, 726; Cano et al., *Trends Biochem. Sci.,* 1995, 20, 117). In a typical MAP kinase pathway, it is thought that a first MAP kinase, called a MEKK, phosphorylates and thereby activates a second MAP kinase, called a MEK, which, in turn, phosphorylates and activates a MAPK/ERK or JNK/SAPK enzyme ("SAPK" is an abbreviation for stress-activated protein kinase). Finally, the activated MAPK/ERK or JNK/SAPK enzyme itself phosphorylates and activates a transcription factor (such as, e.g., AP-1) or other substrates (Cano et al., *Trends Biochem. Sci.,* 1995, 20, 117). This canonical cascade can be simply represented as follows:

MEKK→MEK→MAPK/ERK→transcription factor or JNK/SAPK or other substrate(s)

One of the signal transduction pathways involves the MAP kinases Jun N-terminal kinase 1 (JNK1) and Jun N-terminal kinase 2 (JNK2) which are responsible for the phosphorylation of specific sites (Serine 63 and Serine 73) on the amino terminal portion of c-Jun. Phosphorylation of these sites potentiates the ability of AP-1 to activate transcription (Binetruy et al., *Nature,* 1991, 351, 122; Smeal et al., *Nature,* 1991, 354, 494). Besides JNK1 and JNK2, other JNK family members have been described, including JNK3 (Gupta et al., *EMBO J.,* 1996, 15, 2760), initially named $p49^{3F12}$ kinase (Mohit et al., *Neuron,* 1994, 14, 67). The term "JNK protein" as used herein shall mean a member of the JNK family of kinases, including but not limited to JNK1, JNK2 and JNK3, their isoforms (Gupta et al., *EMBO J.,* 1996, 15, 2760) and other members of the JNK family of proteins whether they function as Jun N-terminal kinases per se (that is, phosphorylate Jun at a specific amino terminally located position) or not.

At least one human leukemia oncogene has been shown to enhance Jun N-terminal kinase function (Raitano et al., *Proc. Natl. Acad. Sci.* (USA), 1995, 92, 11746). Modulation of the expression of one or more JNK proteins is desirable in order to interfere with hyperproliferation of cells and with the transcription of genes stimulated by AP-1 and other JNK protein phosphorylation substrates. Modulation of the expression of one or more other JNK proteins is also desirable in order to interfere with hyperproliferation of cells resulting from abnormalities in specific signal transduction pathways. To date, there are no known therapeutic agents which effectively inhibit gene expression of one or more JNK proteins. Consequently, there remains a long-felt need for improved compositions and methods for modulating the expression of specific JNK proteins.

Moreover, cellular hyperproliferation in an animal can have several outcomes. Internal processes may eliminate hyperproliferative cells before a tumor can form. Tumors are abnormal growths resulting from the hyperproliferation of cells. Cells that proliferate to excess but stay put form benign tumors, which can typically be removed by local surgery. In contrast, malignant tumors or cancers comprise cells that are capable of undergoing metastasis, i.e., a process by which hyperproliferative cells spread to, and secure themselves within, other parts of the body via the circulatory or lymphatic system (see, generally, Chapter 16 In: *Molecular Biology of the Cell,* Alberts et al., eds., Garland Publishing, Inc., New York, 1983). Using antisense oligonucleotides, it has surprisingly been discovered that several genes encoding enzymes required for metastasis are positively regulated by AP-1, which may itself be modulated by antisense oligonucleotides targeted to one or more JNK proteins. Consequently, the invention satisfies the long-felt need for improved compositions and methods for modulating the metastasis of malignant tumors.

SUMMARY OF THE INVENTION

In accordance with the present invention, oligonucleotides are provided which specifically hybridize with a nucleic acid encoding a JNK protein. Certain oligonucleotides of the invention are designed to bind either directly to mRNA transcribed from, or to a selected DNA portion of, a JNK gene that encodes a JNK protein, thereby modulating the expression thereof and/or the phosphorylation of one or more substrates for the JNK protein. Pharmaceutical compositions comprising the oligonucleotides of the invention, and various methods of using the oligonucleotides of the invention, including methods of modulating one or more metastatic events, are also herein provided.

DETAILED DESCRIPTION OF THE INVENTION

Oligonucleotides may comprise nucleotide sequences sufficient in identity and number to effect specific hybridization with a particular nucleic acid. Such oligonucleotides are commonly described as "antisense." Antisense oligonucleotides are commonly used as research reagents, diagnostic aids, and therapeutic agents. It has been discovered that genes (JNK) encoding Jun N-terminal kinase (JNK proteins) are particularly amenable to this approach. In the context of the invention, the terms "Jun N-terminal kinase" and "JNK protein" refer to proteins actually known to phosphorylate the amino terminal (N-terminal) portion of the Jun subunit of AP-1, as well as those that have been tentatively identified as JNK proteins based on amino acid sequence but which may in fact additionally or alternatively bind and/or phosphorylate either other transcription factors (e.g., ATF2) or kinase substrates that are not known to be involved in transcription (Derijard et al., *Cell,* 1994, 76, 1025; Kallunki et al., *Genes & Development,* 1994, 8, 2996; Gupta et al., *EMBO J.,* 1996, 15, 2760). More specifically, the present invention is directed to antisense oligonucleotides that modulate the JNK1, JNK2 and JNK3 proteins. As a consequence of the association between cellular proliferation and activation (via phosphorylation) of AP-1, other transcription factors and/or other proteins by JNK proteins, inhibition of the expression of one or more JNK proteins leads to inhibition of the activation of AP-1 and/or other factors involved in cellular proliferation, cell cycle progression or metastatic events, and, accordingly, results in modulation of these activities. Such modulation is desirable for treating, alleviating or preventing various hyperproliferative disorders or diseases, such as various cancers. Such inhibition is further desirable for preventing or modulating the development of such diseases or disorders in an animal suspected of being, or known to be, prone to such diseases or disorders. If desired, modulation of the expression of one JNK protein can be combined with modulation of one or more additional JNK proteins in order to achieve a requisite level of interference with AP-1-mediated transcription.

Methods of modulating the expression of JNK proteins comprising contacting animals with oligonucleotides specifically hybridizable with a nucleic acid encoding a JNK protein are herein provided. These methods are believed to be useful both therapeutically and diagnostically as a consequence of the association between kinase-mediated activation of AP-1 and cellular proliferation. These methods are also useful as tools, for example, in the detection and determination of the role of kinase-mediated activation of AP-1 in various cell functions and physiological processes and conditions, and for the diagnosis of conditions associated with such expression and activation.

The present invention also comprises methods of inhibiting JNK-mediated activation using the oligonucleotides of the invention. Methods of treating conditions in which abnormal or excessive JNK-mediated cellular proliferation occurs are also provided. These methods employ the oligonucleotides of the invention and are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

The present invention employs oligonucleotides for use in antisense modulation of the function of DNA or messenger RNA (mRNA) encoding a protein the modulation of which is desired, and ultimately to regulate the amount of such a protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expressioat It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with hyperproliferative disorders. The targeting process also includes determination of a site or sites within this gene for the oligonucleotide interaction to occur such that the desired effect, either detection or modulation of expression of the protein, will result. Once the target site or sites have been identified, oligonucleotides are chosen which are sufficiently complementary to the target, i.e., hybridize sufficiently well and with sufficient specificity to give the desired effect. Generally, there are five regions of a gene that may be targeted for antisense modulation: the 5' untranslated region (hereinafter, the "5'-UTR"), the translation initiation codon region (hereinafter, the "tIR"), the open reading frame (hereinafter, the "ORF"), the translation termination codon region (hereinafter, the "tTR") and the 3' untranslated region (hereinafter, the "3'-UTR"). As is known in the art, these regions are arranged in a typical messenger RNA molecule in the following order (left to right, 5' to 3'): 5'-UTR, tIR, ORF, tTR, 3'-UTR. As is known in the art, although some eukaryotic transcripts are directly translated, many ORFs contain one or more sequences, known as "introns," which are excised from a transcript before it is translated; the expressed (unexcised) portions of the ORF are referred to as "exons" (Alberts et al., *Molecular Biology of the Cell,* 1983, Garland Publishing Inc., New York, pp. 411–415). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites.

Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors,* 1990, 4, 45; Gelbert et al., *Somat. Cell. Mol. Genet.,* 1990, 16, 173; Gold and Stormo, in: *Escherichia coli and Salmonella typhimurium: Cellular and Molecular Biology,* Vol. 2, 1987, Neidhardt et al., eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., *Development,* 1995, 121, 3723; Gao et al., *Cancer Res.,* 1995, 55, 743; McDermott et al., *Gene,* 1992, 117, 193; Perri et al., *J. Biol. Chem.,* 1991, 266, 12536; French et al., *J. Virol.,* 1989, 63, 3270; Pushpa-Rekha et al., *J. Biol. Chem.,* 1995, 270, 26993; Monaco et al., *J. Biol. Chem.,* 1994, 269, 347; DeVirgilio et al., *Yeast,* 1992, 8, 1043; Kanagasundaram et al., *Biochim. Biophys. Acta,* 1992, 1171, 198; Olsen et al., *Mol. Endocrinol.,* 1991, 5, 1246; Saul et al., *Appl. Environ. Microbiol.,* 1990, 56, 3117; Yaoita et al., *Proc. Natl. Acad. Sci. USA,* 1990, 87, 7090; Rogers et al., *EMBO J.,* 1990, 9, 2273). In the context of the invention, "start codon" and "translation initiation codon" refer to the codon or codons that are used in vivo to initiate translation of an mRNA molecule transcribed from a gene encoding a JNK protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses from about 25 to about 50 contiguous nucleotides in either direction (i.e., 5' or 3') from a translation initiation codon. Similarly, the terms "stop codon region" and "translation termination region" refer to a portion of such an mRNA or gene that encompasses from about 25 to about 50 contiguous nucleotides in either direction (i.e., 5' or 3') from a translation termination codon.

The remainder of the Detailed Description relates in more detail the (1) Oligonucleotides of the Invention and their (2) Bioequivalents, (3) Utility, (4) Pharmaceutical Compositions and (5) Means of Administration.

1. Oligonucleotides of the Invention

The present invention employs oligonucleotides for use in antisense modulation of one or more JNK proteins. In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of a repeating unit generically known as a nucleotide. The oligonucleotides in accordance with this invention preferably comprise from about 8 to about 30 nucleotides. An unmodified (naturally occurring) nucleotide has three components: (1) a nitrogen-containing heterocyclic base linked by one of its nitrogen atoms to (2) a 5-pentofuranosyl sugar and (3) a phosphate esterified to one of the 5' or 3' carbon atoms of the sugar. When incorporated into an oligonucleotide chain, the phosphate of a first nucleotide is also esterified to an adjacent sugar of a second, adjacent nucleotide via a 3'-5' phosphate linkage. The "backbone" of an unmodified oligonucleotide consists of (2) and (3), that is, sugars linked together by phosphodiester linkages between the 5' carbon of the sugar of a first nucleotide and the 3' carbon of a second, adjacent nucleotide. A "nucleoside" is the combination of (1) a nucleobase and (2) a sugar in the absence of (3) a phosphate moiety (Kornberg, A., *DNA Replication,* W.H. Freeman & Co., San Francisco, 1980, pages 4–7). The backbone of an oligonucleotide positions a series of bases in a specific order; the written representation of this series of bases, which is conventionally written in 5' to 3' order, is known as a nucleotide sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. An oligonucleotide is specifically hybridizable to its target sequence due to the formation of base pairs between specific partner nucleobases in the interior of a nucleic acid duplex. Among the naturally occurring nucleobases, guanine (G) binds to cytosine (C), and adenine (A) binds to thymine (T) or uracil (U). In addition to the equivalency of U (RNA) and T (DNA) as partners for A, other naturally occurring nucleobase equivalents are known, including 5-methylcytosine, 5-hydroxymethylcytosine (HMC), glycosyl HMC and gentiobiosyl HMC (C equivalents), and 5-hydroxymethyluracil (U equivalent). Furthermore, synthetic nucleobases which retain partner specificity are known in the art and include, for example, 7-deaza-Guanine, which retains partner specificity for C. Thus, an oligonucleotide's capacity to specifically hybridize with its target sequence will not be altered by any chemical modification to a nucleobase in the nucleotide sequence of the oligonucleotide which does not significantly effect its specificity for the partner nucleobase in the target oligonucleotide. It is understood in the art that an oligonucleotide need not be 100% complementary to its target DNA sequence to be specifically hybridizable. An oligonucleotide is specifically hybridizable when there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses.

A. Modified Linkages

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science*, 1991, 254:1497; U.S. Pat. No. 5,539,082).

B. Modified Nucleobases

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 2-aminoadenine, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine (Kornberg, A., *DNA Replication*, W.H. Freeman & Co., San Francisco, 1980, pages 75–77; Gebeyehu, G., et al., *Nucleic Acids Res.*, 1987, 15, 4513).

C. Sugar Modifications

The oligonucleotides of the invention may additionally or alternatively comprise substitutions of the sugar portion of the individual nucleotides. For example, oligonucleotides may also have sugar mimetics such as cyclobutyls in place of the pentofuranosyl group. Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'—O—$CH_2CH_2OCH_3$, also known as 2'—O—(2-methoxyethyl)] (Martin et al., *Helv. Chim. Acta*, 1995, 78:486). Other preferred modifications include 2'-methoxy-(2'—O—$CH_3$), 2'-propoxy- (2'—$OCH_2CH_2CH_3$) and 2'-fluoro- (2'-F).

D. Other Modifications

Similar modifications may also be made at other positions on the oligonucleotide, particularly the 3' position of the sugar on the 3' terminal nucleotide and the 5' position of 5' terminal nucleotide. The 5' and 3' termini of an oligonucleotide may also be modified to serve as points of chemical conjugation of, e.g., lipophilic moieties (see immediately subsequent paragraph), intercalating agents (Kuyavin et al., WO 96/32496, published Oct. 17, 1996; Nguyen et al., U.S. Pat. No. 4,835,263, issued May 30, 1989) or hydroxyalkyl groups (Helene et al., WO 96/34008, published Oct. 31, 1996).

Other positions within an oligonucleotide of the invention can be used to chemically link thereto one or more effector groups to form an oligonucleotide conjugate. An "effector group" is a chemical moiety that is capable of carrying out a particular chemical or biological function. Examples of such effector groups include, but are not limited to, an RNA cleaving group, a reporter group, an intercalator, a group for improving the pharmacokinetic properties of an oligonucleotide, or a group for improving the pharmacodynamic properties of an oligonucleotide and other substituents having similar properties. A variety of chemical linkers may be used to conjugate an effector group to an oligonucleotide of the invention. As an example, U.S. Pat. No. 5,578,718 to Cook et al. discloses methods of attaching an alkylthio linker, which may be further derivatized to include additional groups, to ribofuranosyl positions, nucleosidic base positions, or on internucleoside linkages. Additional methods of conjugating oligonucleotides to various effector groups are known in the art; see, e.g., *Protocols for Oligonucleotide Conjugates* (*Methods in Molecular Biology*, Volume 26) Agrawal, S., ed., Humana Press, Totowa, N.J., 1994.

Another preferred additional or alternative modification of the oligonucleotides of the invention involves chemically linking to the oligonucleotide one or more lipopnilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention (Gebeyehu, G., et al., *Nucleic Acids Res.*, 1987, 15:4513). Such lipophilic moieties include but are not limited to a cholesteryl moiety (Letsinger et al., *Proc. Natl. Acad. Sci. U.S.A.*, 1989, 86:6553), cholic acid (Manoharan et al., *Bioorg. Med. Chem. Let.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Oligonucleotides comprising lipophilic moieties, and methods for preparing such oligonucleotides, are disclosed in U.S. Pat. Nos. 5,138,045, 5,218,105 and 5,459,255.

The present invention also includes oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoamidate or phosphotriester linkages (Cook, U.S. Pat. Nos. 5,212,295 and 5,521,302).

E. Chimeric Oligonucleotides

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy- substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2'-methoxyethoxy- substituted), or vice-versa.

F. Synthesis

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

1. Teachings regarding the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,618, issued Jun. 29, 1993, and 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

2. 5-methyl-cytosine

In 2'-methoxyethoxy-modified oligonucleotides, 5-methyl-2'-methoxyethoxy-cytosine residues are used and are prepared as follows.

(a) 2,2'-Anhydro [1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

(b) 2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155°–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

(c) 2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

(d) 3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approximately 90% product). The residue was purified on a 3.5 kg silica gel column and eluted using EtOAc/Hexane (4:1). Pure product fractions were evaporated to yield 96 g (846).

(e) 3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0°–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

(f) 2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. Methanol (400 mL) saturated with $NH_3$ gas was added and the vessel heated to 100° C. for 2 hours (thin layer chromatography, tlc, showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

(g) $N^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

(h) $N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)-phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL) The aqueous washes were back-extracted with $CH_2Cl_2$ (300 mL) and the extracts were combined, dried over $MgSO_4$ and concentrated. The residue obtained was chromatographed on a 1.5 kg silica column using EtOAcHexane (3:1) as the eluting solvent. The pure fractions were combined to give 90.6 g (87%) of the title compound.

2. Bioequivalents

The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to "prodrugs" and "pharmaceutically acceptable salts" of the oligonucleotides of the invention, pharmaceutically acceptable salts of such prodrugs, and other bioequivalents.

A. Oligonucleotide Prodrugs

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

B. Pharmaceutically Acceptable Salts

The term "pharmaceutically acceptable salts" refers to physiologically and pharmaceutically acceptable salts of the oligonucleotides of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for examplwith glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

3. Exemplary Utilities of the Invention

The oligonucteotides of the present invention specifically hybridize to nucleic acids (e.g., mRNAs) encoding a JNK protein. The oligonucleotides of the present invention can be utilized as therapeutic compounds, as diagnostic tools or research reagents that can be incorporated into kits, and in purifications and cellular product preparations, as well as other methodologies, which are appreciated by persons of ordinary skill in the art.

A. Assays and Diagnostic Applications

The oligonucleotides of the present invention can be used to detect the presence of JNK protein-specific nucleic acids in a cell or tissue sample. For example, radiolabeled oligonucleotides can be prepared by $^{32}$P labeling at the 5' end with polynucleotide kinase. (Sambrook et al., *Molecular Cloning. A Laboratory Manual,* Cold Spring Harbor Laboratory Press, 1989, Volume 2, pg. 10.59.) Radiolabeled oligonucleotides are then contacted with cell or tissue samples suspected of containing JNK protein message RNAs (and thus JNK proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of JNK proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a JNK protein gene. Quantitation of the silver grains permits detection of the expression of mRNA molecules encoding these proteins and permits targeting of oligonucleotides to these areas.

Analogous assays for fluorescent detection of expression of JNK protein nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va. Other means of labeling oligonucleotides are known in the art (see, e.g., Ruth, Chapter 6 In: *Methods in Molecular Biology,* Vol. 26: *Protocols for oligonucleotide Conjugates,* Agrawal, ed., Humana Press Inc., Totowa, N.J., 1994, pages 167–185).

Kits for detecting the presence or absence of expression of a JNK protein may also be prepared. Such kits include an oligonucleotide targeted to an appropriate gene, i.e., a gene encoding a JNK protein. Appropriate kit and assay formats, such as, e.g., "sandwich" assays, are known in the art and can easily be adapted for use with the oligonucleotides of the invention. Hybridization of the oligonucleotides of the invention with a nucleic acid encoding a JNK protein can be detected by means known in the art. Such means may include conjugation of an enzyme to the oligonucleotide, radiolabelling of the oligonucleotide or any other suitable detection systems.

B. Protein Purifications

The oligonucleotides of the invention are also useful for the purification of specific Jun kinase proteins from cells that normally express a set of JNK proteins which are similar to each other in terms of their polypeptide sequences and biochemical properties. As an example, the purification of a JNK1 protein from cells that expresses JNK1, JNK2 and JNK3 proteins can be enhanced by first treating such cells with oligonucleotides that inhibit the expression of JNK2 and JNK3 and/or with oligonucleotides that increase the expression of JNK1, because such treatments will increase the relative ratio of JNK1 relative to JNK2 and JNK3. As a result, the yield of JNK1 from subsequent purification steps will be improved as the amount of the biochemically similar (and thus likely to contaminate) JNK2 and JNK3 proteins in extracts prepared from cells so treated will be diminished.

C. Biologically Active Oligonucleotides

The invention is also drawn to the administration of oligonucleotides having biological activity to cultured cells, isolated tissues and organs and animals. By "having biological activity," it is meant that the oligonucleotide functions to modulate the expression of one or more genes in cultured cells, isolated tissues or organs and/or animals. Such modulation can be achieved by an antisense oligonucleotide by a variety of mechanisms known in the art, including but not limited to transcriptional arrest; effects on RNA processing (capping, polyadenylation and splicing) and transportation; enhancement of cellular degradation of the target nucleic acid; and translational arrest (Crooke et al., *Exp. Opin. Ther. Patents,* 1996, 6:855).

In an animal other than a human, the compositions and methods of the invention can be used to study the function of one or more genes in the animal. For example, antisense oligonucleotides have been systemically administered to rats in order to study the role of the N-methyl-D-aspartate receptor in neuronal death, to mice in order to investigate the biological role of protein kinase C-α, and to rats in order to examine the role of the neuropeptide Y1 receptor in anxiety (Wahlestedt et al., *Nature,* 1993, 363:260; Dean et al., *Proc. Natl. Acad. Sci. U.S.A.,* 1994, 91:11762; and Wahlestedt et al., *Science,* 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.,* 1994, 15:250).

The compositions and methods of the invention also have therapeutic uses in an animal, including a human, having (i.e., suffering from), or known to be or suspected of being prone to having, a disease or disorder that is treatable in whole or in part with one or more nucleic acids. The term "therapeutic uses" is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention.

For therapeutic uses, an animal suspected of having a disease or disorder which can be treated or prevented by modulating the expression or activity of a JNK protein is, for example, treated by administering oligonucleotides in accordance with this invention. The oligonucleotides of the invention can be utilized in pharmaceutical compositions by adding an effective amount of an oligonucleotide to a suitable pharmaceutically acceptable carrier such as, e.g., a diluent. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans. The following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections.

As used herein, the term "disease or disorder" (1) includes any abnormal condition of an organism or part, especially as a consequence of infection, inherent weakness, environmental stress, that impairs normal physiological functioning; (2) excludes pregnancy per se but not autoimmune and other diseases associated with pregnancy; and (3) includes cancers and tumors. The term "known to be or suspected of being prone to having a disease or disorder" indicates that the subject animal has been determined to be, or is suspected of being, at increased risk, relative to the general population of such animals, of developing a particular disease or disorder as herein defined. For example, a subject animal "known to be or suspected of being prone to having a disease or disorder" could have a personal and/or family medical history that includes frequent occurrences of a particular disease or disorder. As another example, a subject animal "known to be or suspected of being prone to having a disease or disorder" could have had such a susceptibility determined by genetic screening according to techniques known in the art (see, e.g., U.S. Congress, Office of Technology Assessment, Chapter 5 In: *Genetic Monitoring and Screening in the Workplace,* OTA-BA-455, U.S. Government Printing Office, Washington, D.C., 1990, pages 75–99). The term "a disease or disorder that is treatable in whole or in part with one or more nucleic acids" refers to a disease or disorder, as herein defined, (1) the management, modulation or treatment thereof, and/or (2) therapeutic, curative, palliative and/or prophylactic relief therefrom, can be provided via the administration of an antisense oligonucleotide.

4. Pharmaceutical Compositions

The formulation of pharmaceutical compositions comprising the oligonucleotides of the invention, and their subsequent administration, are believed to be within the skill of those in the art.

A. Therapeutic Considerations

In general, for therapeutic applications, a patient (i.e., an animal, including a human, having or predisposed to a disease or disorder) is administered one or more oligonucleotides, in accordance with the invention in a pharmaceutically acceptable carrier in doses ranging from 0.01 µg to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. In the context of the invention, the term "treatment regimen" is meant to encompass therapeutic, palliative and prophylactic modalities. Following treatment, the patient is monitored for changes in his/her condition and for alleviation of the symptoms of the disorder or disease state. The dosage of the nucleic acid may either be increased in the event the patient does not respond significantly to current dosage levels, or the dose may be decreased if an alleviation of the symptoms of the disorder or disease state is observed, or if the disorder or disease state has been ablated.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. An optimal dosing schedule is used to deliver a therapeutically effective amount of the oligonucleotide being administered via a particular mode of administration.

The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: *Goodman & Gilman's The Pharmacological Basis of Therapeutics,* 9th Ed., Hardman et al., eds., McGraw-Hill, New York, N.Y., 1996).

As used herein, the term "high risk individual" is meant to refer to an individual for whom it has been determined, via, e.g., individual or family history or genetic testing, has a significantly higher than normal probability of being susceptible to the onset or recurrence of a disease or disorder. As art of treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual.

Following successful treatment, it may be desirable to have the patient undergo maintenance therapy to prevent the recurrence of the disease state, wherein the nucleic acid is administered in maintenance doses, ranging from 0.01 μg to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 μg to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, *The Merck Manual of Diagnosis and Therapy,* 15th Ed., pp. 1206–1228, Berkow et al., eds., Rahay, N.J., 1987). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

In another preferred embodiment of the invention, a first antisense oligonucleotide targeted to a first JNK protein is used in combination with a second antisense oligonucleotide targeted to a second JNK protein in order to such JNK proteins to a more extensive degree than can be achieved when either oligonucleotide is used individually. In various embodiments of the invention, the first and second JNK proteins which are targeted by such oligonucleotides are identical, are different JNK proteins or are different isoforms of the same JNK protein.

B. Pharmaceutical Compositions

Pharmaceutical compositions for the non-parenteral administration of oligonucleotides may include sterile aqueous solutions which may also contain buffers, diluents and other suitable additives. Pharmaceutically acceptable organic or inorganic carrier substances suitable for non-parenteral administration which do not deleteriously react with oligonucleotides can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The pharmaceutical compositions can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with the oligonucleotide(s) of the pharmaceutical composition. Pharmaceutical compositions in the form of aqueous suspensions may contain substances which increase the viscosity of the suspension including, for example, sodium carboxymethylcellulose, sorbitol and/or dextran. Optionally, such suspensions may also contain stabilizers.

In one embodiment of the invention, an oligonucleotide is administered via the rectal mode. In particular, pharmaceutical compositions for rectal administration include foams, solutions (enemas) and suppositories. Rectal suppositories for adults are usually tapered at one or both ends and typically weigh about 2 g each, with infant rectal suppositories typically weighing about one-half as much, when the usual base, cocoa butter, is used (Block, Chapter 87 In: *Remington's Pharmaceutical Sciences,* 18th Ed., Gennaro, ed., Mack Publishing Co., Easton, Pa., 1990).

In a preferred embodiment of the invention, one or more oligonucleotides are administered via oral delivery. Pharmaceutical compositions for oral administration including powders or granules, suspensions or solutions in water or non-aqueous media, capsules, sachets, troches, tablets or SECs (soft elastic capsules or "caplets"). Thickeners, flavoring agents, diluents, emulsifiers, dispersing aids, carrier substances or binders may be desirably added to such pharmaceutical compositions. The use of such pharmaceutical compositions has the effect of delivering the oligonucleotide to the alimentary canal for exposure to the mucosa thereof. Accordingly, the pharmaceutical composition can comprise material effective in protecting the oligonucleotide from pH extremes of the stomach, or in releasing the oligonucleotide over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing pharmaceutical compositions for alimentary delivery are well known in the art. See, generally, Nairn, Chapter 83; Block, Chapter 87; Rudnic et al., Chapter 89; Porter, Chapter 90; and Longer et al., Chapter 91 In: *Remington's Pharmaceutical Sciences*, 18th Ed., Gennaro, ed., Mack Publishing Co., Easton, Pa., 1990. The oligonucleotides of the invention can be incorporated in a known manner into customary pharmaceutical compositions, such as tablets, coated tablets, pills, granules, aerosols, syrups, emulsions, suspensions and solutions, using inert, non-toxic, pharmaceutically acceptable carriers (excipients). The therapeutically active compound should in each case be present here in a concentration of about 0.5% to about 95% by weight of the total mixture, i.e., in amounts which are sufficient to achieve the stated dosage range. The pharmaceutical compositions are prepared, for example, by diluting the active compounds with pharmaceutically acceptable carriers, if appropriate using emulsifying agents and/or dispersing agents, and, for example, in the case where water is used as the diluent, organic solvents can be used as auxiliary solvents if appropriate. Pharmaceutical compositions may be formulated in a conventional manner using additional pharmaceutically acceptable carriers as appropriate. Thus, the compositions may be prepared by conventional means with additional excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

The pharmaceutical compositions, which may conveniently be presented in unit dosage form, may be prepared according to conventional techniques well known in the pharmaceutical industry. Such techniques include the step of bringing into association the active ingredient(s) with the pharmaceutically acceptable carrier(s). In general the pharmaceutical compositions are prepared by uniformly and intimately bringing into association the active ingredient(s) with liquid excipients or finely divided solid excipients or both, and then, if necessary, shaping the product.

Pharmaceutical compositions of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein. Pharmaceutical compositions for parenteral, intrathecal or intraventricular administration, or colloidal dispersion systems, may include sterile aqueous solutions which may also contain buffers, diluents and other suitable additives.

C. Penetration Enhancers

Pharmaceutical compositions comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8:91–192; Muranishi, *Critical Reviews in Therapeutic Drug Carrier Systems*, 1990, 7:1).

1. Fatty Acids

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, page 92; Muranishi, *Critical Reviews in Therapeutic Drug Carrier Systems*, 1990, 7:1; El-Hariri et al., *J. Pharm. Pharmacol.*, 1992, 44:651).

2. Bile Salts

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

3. Chelating Agents

Chelating agents have the added advantage of also serving as DNase inhibitors and include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7:1; Buur et al., *J. Control Rel.*, 1990, 14:43).

4. Surfactants

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorochemical emulsions, such as FC-43 (Takahashi et al., *J. Pharm. Phamacol.*, 1988, 40:252).

5. Non-Surfactants

Non-surfactants include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.,* 1987, 39:621).

D. Carrier Compounds

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.,* 1995, 5:115; Takakura et al., *Antisense & Nucl. Acid Drug Dev.,* 1996, 6:177).

E. Pharmaceutically Acceptable Carriers

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

F. Miscellaneous Additional Components

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacities, thickening agents and stabilizers. However, such materials, when added, should not unduly interfere with the biological activities of the components of the compositions of the invention.

G. Colloidal Dispersion Systems

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles and liposomes. A preferred colloidal dispersion system is a plurality of liposomes, artificial membrane vesicles which may be used as cellular delivery vehicles for bioactive agents in vitro and in vivo (Mannino et al., *Biotechniques,* 1988, 6, 682; Blume and Cevc, *Biochem. et Biophys. Acta,* 1990, 1029, 91; Lappalainen et al., *Antiviral Res.,* 1994, 23, 119; Chonn and Cullis, *Current Op. Biotech.,* 1995, 6, 698). It has been shown that large unilamellar vesicles (LUV), which range in size from 0.2–0.4 $\mu$m, can encapsulate a substantial percentage of an aqueous buffer containing large macromolecules. RNA, DNA and intact virions can be encapsulated within the aqueous interior and delivered to brain cells in a biologically active form (Fraley et al., *Trends Biochem. Sci.,* 1981, 6, 77). The composition of the liposome is usually a combination of lipids, particularly phospholipids, in particular, high phase transition temperature phospholipids, usually in combination with one or more steroids, particularly cholesterol. Examples of lipids useful in liposome production include phosphatidyl compounds, such as phosphatidylglycerol, phosphatidylcholine, phosphatidylserine, sphingolipids, phosphatidylethanolamine, cerebrosides and gangliosides. Particularly useful are diacyl phosphatidylglycerols, where the lipid moiety contains from 14–18 carbon atoms, particularly from 16–18 carbon atoms, and is saturated (lacking double bonds within the 14–18 carbon atom chain). Illustrative phospholipids include phosphatidylcholine, dipalmitoylphosphatidylcholine and distearoylphosphatidylcholine.

The targeting of colloidal dispersion systems, including liposomes, can be either passive or active. Passive targeting utilizes the natural tendency of liposomes to distribute to cells of the reticuloendothelial system in organs that contain sinusoidal capillaries. Active targeting, by contrast, involves modification of the liposome by coupling thereto a specific ligand such as a viral protein coat (Morishita et al., *Proc. Natl. Acad. Sci.* (U.S.A.), 1993, 90, 8474), monoclonal antibody (or a suitable binding portion thereof), sugar, glycolipid or protein (or a suitable oligopeptide fragment thereof), or by changing the composition and/or size of the liposome in order to achieve distribution to organs and cell types other than the naturally occurring sites of localization. The surface of the targeted colloidal dispersion system can be modified in a variety of ways. In the case of a liposomal targeted delivery system, lipid groups can be incorporated into the lipid bilayer of the liposome in order to maintain the targeting ligand in close association with the lipid bilayer. Various linking groups can be used for joining the lipid chains to the targeting ligand. The targeting ligand, which binds a specific cell surface molecule found predominantly on cells to which delivery of the oligonucleotides of the invention is desired, may be, for example, (1) a hormone, growth factor or a suitable oligopeptide fragment thereof which is bound by a specific cellular receptor predominantly expressed by cells to which delivery is desired or (2) a polyclonal or monoclonal antibody, or a suitable fragment thereof (e.g., Fab; F(ab')$_2$) which specifically binds an antigenic epitope found predominantly on targeted cells. Two or more bioactive agents (e.g., an oligonucleotide and a conventional drug; two oligonucleotides) can be combined within, and delivered by, a single liposome. It is also possible to add agents to colloidal dispersion systems which enhance the intercellular stability and/or targeting of the contents thereof.

5. Means of Administration

The present invention provides compositions comprising oligonucleotides intended for administration to an animal. For purposes of the invention, unless otherwise specified, the term "animal" is meant to encompass humans as well as other mammals, as well as reptiles, amphibians, and birds.

A. Parenteral Delivery

The term "parenteral delivery" refers to the administration of an oligonucleotide of the invention to an animal in a manner other than through the digestive canal. Means of preparing and administering parenteral pharmaceutical compositions are known in the art (see, e.g., Avis, Chapter 84 In: *Remington's Pharmaceutical Sciences*, 18th Ed., Gennaro, ed., Mack Publishing Co., Easton, Pa., 1990, pages 1545–1569). Parenteral means of delivery include, but are not limited to, the following illustrative examples.

1. Intravitreal injection

For the direct delivery of drug to the vitreous humor of a mammalian eye, is described in U.S. Pat. No. 5,591,720, the contents of which are hereby incorporated by reference. Means of preparing and administering ophthalmic preparations are known in the art (see, e.g., Mullins et al., Chapter 86 In: *Remington's Pharmaceutical Sciences*, 18th Ed., Gennaro, ed., Mack Publishing Co., Easton, Pa., 1990, pages 1581–1595).

2. Intravenous administration

Of antisense oligonucleotides to various non-human mammals has been described by Iversen (Chapter 26 In: Antisense Research and Applications, Crooke et al., eds., CRC Press, Boca Raton, Fla. 1993, pages 461–469). Systemic delivery of oligonucleotides to non-human mammals via intraperitoneal means has also been described (Dean et al., *Proc. Natl. Acad. Sci. (U.S.A.)*, 1994, 91, 11766).

3. Intraluminal drug administration

For the direct delivery of drug to an isolated portion of a tubular organ or tissue (e.g., such as an artery, vein, ureter or urethra), may be desired for the treatment of patients with diseases or conditions afflicting the lumen of such organs or tissues. To effect this mode of oligonucleotide administration, a catheter or cannula is surgically introduced by appropriate means. For example, for treatment of the left common carotid artery, a cannula is inserted thereinto via the external carotid artery. After isolation of a portion of the tubular organ or tissue for which treatment is sought, a composition comprising the oligonucleotides of the invention is infused through the cannula or catheter into the isolated segment. After incubation for from about 1 to about 120 minutes, during which the oligonucleotide is taken up by cells of the interior lumen of the vessel, the infusion cannula or catheter is removed and flow within the tubular organ or tissue is restored by removal of the ligatures which effected the isolation of a segment thereof (Morishita et al., *Proc. Natl. Acad. Sci. U.S.A.*, 1993, 90, 8474). Antisense oligonucleotides may also be combined with a biocompatible matrix, such as a hydrogel material, and applied directly to vascular tissue in vivo (Rosenberg et al., U.S. Pat. No. 5,593,974, issued Jan. 14, 1997).

4. Intraventricular drug administration

For the direct delivery of drug to the brain of a patient, may be desired for the treatment of patients with diseases or conditions afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., *Cancer Research*, 1984, 44, 1698; Shaw, *Cancer*, 1993, 72(11 Suppl.), 3416). The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and the dose of drug to be administered, ranging from 0.01 $\mu$g to 100 g per kg of body weight, the pump reservoir may be refilled at 3–10 week intervals. Refilling of the pump is accomplished by percutaneous puncture of the self-sealing septum of the pump.

5. Intrathecal drug administration

For the introduction of a drug into the spinal column of a patient may be desired for the treatment of patients with diseases of the central nervous system. To effect this route of oligonucleotide administration, a silicon catheter is surgically implanted into the L3–4 lumbar spinal interspace of a human patient, and is connected to a subcutaneous infusion pump which has been surgically implanted in the upper abdominal region (Luer and Hatton, *The Annals of Pharmacotherapy*, 1993, 27, 912; Ettinger et al., 1978, *Cancer*, 41, 1270, 1978; Yaida et al., *Regul. Pept.*, 1995, 59, 193). The pump is used to inject the oligonucleotides and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 $\mu$g to 100 g per kg of body weight, the pump reservoir may be refilled at 3–10 week intervals. Refilling of the pump is accomplished by a single percutaneous puncture to the self-sealing septum of the pump. The distribution, stability and pharmacokinetics of oligonucleotides within the central nervous system may be followed according to known methods (Whitesell et al., *Proc. Natl. Acad. Sci.* (USA), 1993, 90, 4665).

To effect delivery of oligonucleotides to areas other than the brain or spinal column via this method, the silicon catheter is configured to connect the subcutaneous infusion pump to, e.g., the hepatic artery, for delivery to the liver (Kemeny et al., *Cancer*, 1993, 71, 1964). Infusion pumps may also be used to effect systemic delivery of oligonucleotides (Ewel et al., *Cancer Research*, 1992, 52, 3005; Rubenstein et al., *J. Surg. Oncol.*, 1996, 62, 194).

6. Epidermal and Transdermal Delivery

In which pharmaceutical compositions containing drugs are applied topically, can be used to administer drugs to be absorbed by the local dermis or for further penetration and absorption by underlying tissues, respectively. Means of preparing and administering medications topically are known in the art (see, e.g., Block, Chapter 87 In: *Remington's Pharmaceutical Sciences*, 18th Ed., Gennaro, ed., Mack Publishing Co., Easton, Pa., 1990, pages 1596–1609).

7. Vaginal Delivery

Provides local treatment and avoids first pass metabolism, degradation by digestive enzymes, and potential systemic side-effects. This mode of administration may be preferred for antisense oligonucleotides targeted to pathogenic organisms for which the vagina is the usual habitat, e.g., *Trichomonas vaginalis*. In another embodiment, antisense oligonucleotides to genes encoding sperm-specific antibodies can be delivered by this mode of administration in order to increase the probability of conception and subsequent pregnancy. Vaginal suppositories (Block, Chapter 87 In: *Remington's Pharmaceutical Sciences*, 18th Ed., Gennaro, ed., Mack Publishing Co., Easton, Pa., 1990, pages 1609–1614) or topical ointments can be used to effect this mode of delivery.

8. Intravesical Delivery

Provides local treatment and avoids first pass metabolism, degradation by digestive enzymes, and potential systemic side-effects. However, the method requires urethral catheterization of the patient and a skilled staff. Nevertheless, this mode of administration may be preferred for antisense oligonucleotides targeted to pathogenic organisms, such as *T. vaginalis*, which may invade the urogenital tract.

B. Alimentary Delivery

The term "alimentary delivery" refers to the administration, directly or otherwise, to a portion of the alimentary canal of an animal. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastrointestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the nucleic acid(s) so administered.

1. Buccal/Sublingual Administration

Delivery of a drug via the oral mucosa has several desirable features, including, in many instances, a more rapid rise in plasma concentration of the drug than via oral delivery (Harvey, Chapter 35 In: *Remington's Pharmaceutical Sciences*, 18th Ed., Gennaro, ed., Mack Publishing Co., Easton, Pa., 1990, page 711). Furthermore, because venous drainage from the mouth is to the superior vena cava, this route also bypasses rapid first-pass metabolism by the liver. Both of these features contribute to the sublingual route being the mode of choice for nitroglycerin (Benet et al., Chapter 1 In: *Goodman & Gilman's The Pharmacological Basis of Therapeutics*, 9th Ed., Hardman et al., eds., McGraw-Hill, New York, N.Y., 1996, page 7).

2. Endoscopic Administration

Endoscopy can be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., Gan To Kagaku Ryoho, 1992, 19(10 Suppl.):1591). However, the procedure is unpleasant for the patient, and requires a highly skilled staff.

3. Rectal Administration

Drugs administered by the oral route can often be alternatively administered by the lower enteral route, i.e., through the anal portal into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration may result in more prompt and higher blood levels than the oral route, but the converse may be true as well (Harvey, Chapter 35 In: *Remington's Pharmaceutical Sciences*, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 In: *Goodman & Gilman's The Pharmacological Basis of Therapeutics*, 9th Ed., Hardman et al., eds., McGraw-Hill, New York, N.Y., 1996).

4. Oral Administration

The preferred method of administration is oral delivery, which is typically the most convenient route for access to the systemic circulation. Absorption from the alimentary canal is governed by factors that are generally applicable, e.g., surface area for absorption, blood flow to the site of absorption, the physical state of the drug and its concentration at the site of absorption (Benet et al., Chapter 1 In: *Goodman & Gilman's The Pharmacological Basis of Therapeutics*, 9th Ed., Hardman et al., eds., McGraw-Hill, New York, N.Y., 1996, pages 5–7). A significant factor which may limit the oral bioavailability of a drug is the degree of "first pass effects." For example, some substances have such a rapid hepatic uptake that only a fraction of the material absorbed enters the peripheral blood (Van Berge-Henegouwen et al., *Gastroenterology*, 1977, 73:300). The compositions and methods of the invention circumvent, at least partially, such first pass effects by providing improved uptake of nucleic acids and thereby, e.g., causing the hepatic uptake system to become saturated and allowing a significant portion of the nucleic acid so administered to reach the peripheral circulation. Additionally or alternatively, the hepatic uptake system is saturated with one or more inactive carrier compounds prior to administration of the active nucleic acid.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

Example 1

Synthesis of Oligonucleotides

A. General Synthetic Techniques

Oligonucleotides were synthesized on an automated DNA synthesizer using standard phosphoramidite chemistry with oxidation using iodine. β-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages.

The synthesis of 2'-O-methyl- (a.k.a. 2'-methoxy-) phosphorothioate oligonucleotides is according to the procedures set forth above substituting 2'-O-methyl β-cyanoethyldiisopropyl phosphoramidites (Chemgenes, Needham, Ma.) for standard phosphoramidites and increasing the wait cycle after the pulse delivery of tetrazole and base to 360 seconds.

Similarly, 2'-O-propyl- (a.k.a 2'-propoxy-) phosphorothioate oligonucleotides are prepared by slight modifications of this procedure and essentially according to procedures disclosed in U.S. patent application Ser. No. 08/383, 666, filed Feb. 3, 1995, which is assigned to the same assignee as the instant application.

The 2'-fluoro-phosphorothioate oligonucleotides of the invention are synthesized using 5'-dimethoxytrityl-3'-phosphoramidites and prepared as disclosed in U.S. patent application Ser. No. 08/383,666, filed Feb. 3, 1995, and U.S. Pat. No. 5,459,255, which issued Oct. 8, 1996, both of which are assigned to the same assignee as the instant application.

The 2'-fluoro-oligonucleotides were prepared using phosphoramidite chemistry and a slight modification of the standard DNA synthesis protocol (i.e., deprotection was effected using methanolic ammonia at room temperature).

The 2'-methoxyethoxy oligonucleotides were synthesized essentially according to the methods of Martin et al. (*Helv. Chim. Acta,* 1995, 78, 486). For ease of synthesis, the 3' nucleotide of the 2'-methoxyethoxy oligonucleotides was a deoxynucleotide, and 2'—O—CH$_2$CH$_2$OCH$_3$ cytosines were 5-methyl cytosines, which were synthesized according to the procedures described below.

PNA antisense analogs are prepared essentially as described in U.S. Pat. Nos. 5,539,082 and 5,539,083, both of which (1) issued Jul. 23, 1996, and (2) are assigned to the same assignee as the instant application.

B. Purification

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Trisborate buffer, pH 7.0. Oligodeoxynucleotides and their phosphorothioate analogs were judged from electrophoresis to be greater than 80% full length material.

Example 2

Assays for Oligonucleotide-Mediated Inhibition of JNK mRNA Expression in Human Tumor Cells In order to evaluate the activity of potential JNK-modulating oligonucleotides, human lung carcinoma cell line A549 (American Type Culture Collection, Rockville, Md. No. ATCC CCL-185) cells were grown and treated with oligonucleotides or control solutions as detailed below. After harvesting, cellular extracts were prepared and examined for specific JNK mRNA levels or JNK protein levels (i.e., Northern or Western assays, respectively). In all cases, "% expression" refers to the amount of JNK-specific signal in an oligonucleotide-treated cell relative to an untreated cell (or a cell treated with a control solution that lacks oligonucleotide), and "% inhibition" is calculated as 100%−% Expression=% Inhibition.

Northern Assays

The mRNA expression of each JNK protein was determined by using a nucleic acid probe specifically hybridizable thereto. Nucleic acid probes specific for JNK1, JNK2 and JNK3 are described in Examples 3, 4 and 5, respectively. The probes were radiolabelled by means well known in the art (see, e.g., *Short Protocols in Molecular Biology,* 2nd Ed., Ausubel et al., eds., John Wiley & Sons, New York, 1992, pages 3–11 to 2–3–44 and 4–17 to 4–18; Ruth, Chapter 6 In: *Methods in Molecular Biology,* Vol. 26: *Protocols for Oligonucleotide Conjugates,* Agrawal, ed., Humana Press Inc., Totowa, N.J., 1994, pages 167–185; and Chapter 10 In: *Molecular Cloning: A Laboratory Manual,* 2nd Ed., Sambrook et al., eds., pages 10.1–10.70). The blots were stripped and reprobed with a $^{32}$P-labeled glyceraldehyde 3-phosphate dehydrogenase (G3PDH) probe (Clontech Laboratories, Inc., Palo Alto, Calif.) in order to confirm equal loading of RNA and to allow the levels of JNK transcripts to be normalized with regard to the G3PDH signals.

A549 cells were grown in T-75 flasks until 80–90% confluent. At this time, the cells were washed twice with 10 mL of media (DMEM), followed by the addition of 5 mL of DMEM containing 20 μg/mL of LIPOFECTIN™ (i.e., 1:1 (w/w) DOTMA/DOPE, Life Technologies, Gaithersburg, Md.; DOTMA=N-[1-(2,3-dioleyoxy)propyl]-N,N,N-trimethylammonium chloride; DOPE=dioleoyl phosphatidylethanolamine). The oligonucleotides were added from a 10 μM stock solution to a final concentration of 400 nM, and the two solutions were mixed by swirling the flasks. As a control, cells were treated with LIPOFECTIN™ without oligonucleotide under the same conditions and for the same times as the oligonucleotide-treated samples. After 4 hours at 37° C., the medium was replaced with fresh DMEM containing 10% serum. The cells were allowed to recover for 18 hours. Total cellular RNA was then extracted in guanidinium, subject to gel electrophoresis and transferred to a filter according to techniques known in the art (see, e.g., Chapter 7 In: *Molecular Cloning: A Laboratory Manual,* 2nd Ed., Sambrook et al., eds., pages 7.1–7.87, and *Short Protocols in Molecular Biology,* 2nd Ed., Ausubel et al., eds., John Wiley & Sons, New York, 1992, pages 2–24 to 2–30 and 4–14 to 4–29). Filters were typically hybridized overnight to a probe specific for the particular JNK gene of interest in hybridization buffer (25 mM KPO$_4$, pH 7.4; 5×SSC; 5×Denhardt's solution, 100 μg/ml Salmon sperm DNA and 50% formamide) (Alahari et al., *Nucl. Acids Res.,* 1993, 21, 4079). This was followed by two washes with 1×SSC, 0.1% SDS and two washes with 0.25×SSC, 0.1% SDS. Hybridizing bands were visualized by exposure to X-OMAT AR film and quantitated using a PHOSPHORIMAGER™ essentially according to the manufacturer's instructions (Molecular Dynamics, Sunnyvale, Calif.).

Western Assays

A549 cells were grown and treated with oligonucleotides as described above. Cells were lysed, and protein extracts were electrophoresed (SDS-PAGE) and transferred to nitrocellulose filters by means known in the art (see, e.g., Chapter 18 In: *Molecular Cloning: A Laboratory Manual,* 2nd Ed., Sambrook et al., eds., pages 18.34, 18.47–18.54 and 18.60–18.75)). The amount of each JNK protein was determined by using a primary antibody that specifically recognizes the appropriate JNK protein. The primary antibodies specific for each JNK protein are described in the appropriate Examples. The primary antibodies were detected by means well known in the art (see, e.g., *Short Protocols in Molecular Biology,* 2nd Ed., Ausubel et al., eds., John Wiley & Sons, New York, 1992, pages 10–33 to 10–35; and Chapter 18 In: *Molecular Cloning: A Laboratory Manual,* 2nd Ed., Sambrook et al., eds., pages 18.1–18.75 and 18.86–18.88) and quantitated using a PHOSPHORIMAGER™ essentially according to the manufacturer's instructions (Molecular Dynamics, Sunnyvale, Calif.).

Levels of JNK proteins can also be quantitated by measuring the level of their corresponding kinase activity. Such kinase assays can be done in gels in situ (Hibi et al., *Genes & Dev.,* 1993, 7, 2135) or after immunoprecipitation from cellular extracts (Derijard et al., *Cell,* 1994, 76, 1025). Substrates and/or kits for such assays are commercially available from, for example, Upstate Biotechnology, Inc. (Lake Placid, N.Y.), New England Biolabs, Inc., (Beverly, Mass.) and Calbiochem-Novabiochem Biosciences, Inc., (La Jolla, Calif.).

Example 3

Oligonucleotide-Mediated Inhibition of JNK1 Expression

A. JNK1 oligonucleotide sequences

Table 1 lists the nucleotide sequences of a set of oligonucleotides designed to specifically hybridize to JNK1 mRNAs and their corresponding ISIS and SEQ ID numbers. The nucleotide co-ordinates of the target gene, JNK1, and gene target regions are also included. The nucleotide co-ordinates are derived from GenBank accession No. L26318, locus name "HUMJNK1" (see also FIG. 1(A) of Derijard et al., Cell, 1994, 76, 1025). The abbreviations for gene target regions are as follows: 5'-UTR, 5' untranslated region; tIR, translation initiation region; ORF, open reading frame; 3'-UTR, 3' untranslated region. The nucleotides of the oligonucleotides whose sequences are presented in Table 1 are connected by phosphorothioate linkages and are unmodified at the 2' position (i.e., 2'-deoxy). It should be noted that the oligonucleotide target co-ordinate positions and gene target regions may vary within mRNAs encoding related isoforms of JNK1 (see subsection G, below).

In addition to hybridizing to human JNK1 mRNAs, the full oligonucleotide sequences of ISIS Nos. 12548 (SEQ ID NO: 17) and 12551 (SEQ ID NO: 20) hybridize to the 5' ends of mRNAs from Rattus norvegicus that encode a stress-activated protein kinase named "p54γ" (Kyriakis et al., Nature, 1994, 369, 156). Specifically, ISIS 12548 (SEQ ID NO: 17) hybridizes to bases 498–517 of GenBank accession No. L27129, locus name "RATSAPKD," and ISIS 12551 (SEQ ID NO: 20) hybridizes to bases 803–822 of the same sequence. These oligonucleotides are thus preferred embodiments of the invention for investigating the role of the p54γ protein kinase in rat in vitro, i.e., in cultured cells or tissues derived from whole animals, or in vivo.

B. JNK1-specific probes

In initial screenings of a set of oligonucleotides derived from the JNK1 sequence (Table 2) for biological activity, a cDNA clone of JNK1 (Derijard et al., Cell, 1994, 76, 1025) was radiolabeled and used as a JNK1-specific probe in Northern blots. Alternatively, however, one or more of the oligonucleotides of Table 1 is detectably labeled and used as a JNK1-specific probe.

C. Activities of JNK1 oligonucleotides

The data from screening a set of JNK1-specific phosphorothioate oligonucleotides (Table 2) indicate the following results. Oligonucleotides showing activity in this assay, as reflected by levels of inhibition from ≧about 50% to about 100% of JNK1 mRNA levels, include ISIS Nos. 11982, 11983, 12463, 12464, 12538, 12539, 12548, 12549, 12550, 12552, 12553, 12554, 12555, 12556 and 12557 (SEQ ID NOS: 5, 6, 13, 14, 15, 16, 17, 18, 19, 21, 22, 23, 24, 25 and 26, respectively). These oligonucleotides are thus preferred embodiments of the invention for modulating JNK1 expression. Oligonucleotides showing levels of inhibition of from ≧about 80% to about 100% of JNK1 mRNAs in this assay, include ISIS Nos. 11982, 12539, 12548, 12554 and 12464 (SEQ ID NOS: 5, 16, 17 and 23, respectively). These oligonucleotides are thus more preferred embodiments of the invention for modulating JNK1 expression.

The time course of inhibition of JNK1 mRNA expression by ISIS 12539 (SEQ ID NO: 16) is shown in Table 3. Following the 4 hour treatment with ISIS 12539, the level of inhibition of JNK1 was greater than about 85% (t=0 h), rose to about 95% inhibition at t=4 h, and subsequently remained at greater than or equal to about 80% (t=12 and 48 h) or 60% (t=72 h).

TABLE 2

Activities of JNK1 Oligonucleotides

| ISIS No: | SEQ ID NO: | GENE TARGET REGION | % EXPRESSION: | % INHIBITION: |
|---|---|---|---|---|
| 11978 | 1 | ORF | 85% | 15% |
| 11979 | 2 | ORF | 90% | 10% |
| 11980 | 3 | ORF | 85% | 15% |
| 11981 | 4 | ORF | 62% | 28% |

TABLE 1

Nucleotide Sequences of JNK1 Oligonucleotides

| ISIS NO. | NUCLEOTIDE SEQUENCE (5' -> 3') | SEQ ID NO: | TARGET GENE NUCLEOTIDE CO-ORDINATES | GENE TARGET REGION |
|---|---|---|---|---|
| 11978 | ATT—CTT—TCC—ACT—CTT—CTA—TT | 1 | 1062–1081 | ORF |
| 11979 | CTC—CTC—CAA—GTC—CAT—AAC—TT | 2 | 1094–1113 | ORF |
| 11980 | CCC—GTA—TAA—CTC—CAT—TCT—TG | 3 | 1119–1138 | ORF |
| 11981 | CTG—TGC—TAA—AGG—AGA—GGG—CT | 4 | 1142–1161 | ORF |
| 11982 | ATG—ATG—GAT—GCT—GAG—AGC—CA | 5 | 1178–1197 | 3'-UTR |
| 11983 | GTT—GAC—ATT—GAA—GAC—ACA—TC | 6 | 1215–1234 | 3'-UTR |
| 11984 | CTG—TAT—CAG—AGG—CCA—AAG—TC | 7 | 1241–1260 | 3'-UTR |
| 11985 | TGC—TGC—TTC—TAG—ACT—GCT—GT | 8 | 1261–1280 | 3'-UTR |
| 11986 | AGT—CAT—CTA—CAG—CAG—CCC—AG | 9 | 1290–1309 | 3'-UTR |
| 11987 | CCA—TCC—CTC—CCA—CCC—CCC—GA | 10 | 1320–1339 | 3'-UTR |
| 11988 | ATC—AAT—GAC—TAA—CCG—ACT—CC | 11 | 1340–1359 | 3'-UTR |
| 11989 | CAA—AAA—TAA—GAC—CAC—TGA—AT | 12 | 1378–1397 | 3'-UTR |
| 12463 | CAC—GCT—TGC—TTC—TGC—TCA—TG | 13 | 0018–0037 | tIR |
| 12464 | CGG—CTT—AGC—TTC—TTG—ATT—GC | 14 | 0175–0194 | ORF |
| 12538 | CCC—GCT—TGG—CAT—GAG—TCT—GA | 15 | 0207–0226 | ORF |
| 12539 | CTC—TCT—GTA—GGC—CCG—CTT—GG | 16 | 0218–0237 | ORF |
| 12548 | ATT—TGC—ATC—CAT—GAG—CTC—CA | 17 | 0341–0360 | ORF |
| 12549 | CGT—TCC—TGC—AGT—CCT—GGC—CA | 18 | 0533–0552 | ORF |
| 12550 | GGA—TGA—CCT—CGG—GTG—CTC—TG | 19 | 0591–0610 | ORF |
| 12551 | CCC—ATA—ATG—CAC—CCC—ACA—GA | 20 | 0646–0665 | ORF |
| 12552 | CGG—GTG—TTG—GAG—AGC—TTC—AT | 21 | 0956–0975 | ORF |
| 12553 | TTT—GGT—GGT—GGA—GCT—TCT—GC | 22 | 1006–1025 | ORF |
| 12554 | GGC—TGC—CCC—CGT—ATA—ACT—CC | 23 | 1126–1145 | ORF |
| 12555 | TGC—TAA—AGG—AGA—GGG—CTG—CC | 24 | 1139–1158 | ORF |
| 12556 | AGG—CCA—AAG—TCG—GAT—CTG—TT | 25 | 1232–1251 | 3'-UTR |
| 12557 | CCA—CCC—CCC—GAT—GGC—CCA—AG | 26 | 1311–1330 | 3'-UTR |

TABLE 2-continued

Activities of JNK1 Oligonucleotides

| ISIS No: | SEQ ID NO: | GENE TARGET REGION | % EXPRESSION: | % INHIBITION: |
|---|---|---|---|---|
| 11982 | 5 | 3'-UTR | 13% | 87% |
| 11983 | 6 | 3'-UTR | 40% | 60% |
| 11984 | 7 | 3'-UTR | 53% | 47% |
| 11985 | 8 | 3'-UTR | 47% | 53% |
| 11986 | 9 | 3'-UTR | 90% | 10% |
| 11987 | 10 | 3'-UTR | 47% | 53% |
| 11988 | 11 | 3'-UTR | 78% | 22% |
| 11989 | 12 | 3'-UTR | 60% | 40% |
| 12463 | 13 | tIR | 23% | 77% |
| 12464 | 14 | ORF | 18% | 82% |
| 12538 | 15 | ORF | 33% | 67% |
| 12539 | 16 | ORF | 9% | 91% |
| 12548 | 17 | ORF | 5% | 95% |
| 12549 | 18 | ORF | 28% | 72% |
| 12550 | 19 | ORF | 40% | 60% |
| 12551 | 20 | ORF | 52% | 48% |
| 12552 | 21 | ORF | 34% | 66% |
| 12553 | 22 | ORF | 25% | 75% |
| 12554 | 23 | ORF | 11% | 89% |
| 12555 | 24 | ORF | 27% | 73% |
| 12556 | 25 | 3'-UTR | 41% | 59% |
| 12557 | 26 | 3'-UTR | 29% | 71% |

TABLE 3

Time Course of Response to JNK1 Antisense Oligonucleotides (ASOs)

| ISIS # | SEQ ID NO: | ASO Description | Time | Normalized % Control | % Inhibition |
|---|---|---|---|---|---|
| control | — | (LIPOFECTIN ™ only) | 0 h | 100.0 | 0.0 |
| control | — | " | 4 h | 100.0 | 0.0 |
| control | — | " | 12 h | 100.0 | 0.0 |
| control | — | " | 48 h | 100.0 | 0.0 |
| control | — | " | 72 h | 100.0 | 0.0 |
| 12539 | 16 | JNK1 active | 0 h | 14.1 | 85.9 |
| 12539 | 16 | " | 4 h | 5.9 | 94.1 |
| 12539 | 16 | " | 12 h | 11.6 | 88.4 |
| 12539 | 16 | " | 48 h | 21.0 | 79.0 |
| 12539 | 16 | " | 272 h | 41.5 | 58.5 |

D. Additional JNK1 oligonucleotides

The results for JNK1-specific oligonucleotides (Table 2) indicate that one of the most active phosphorothioate oligonucleotides for modulating JNK1 expression is ISIS 12539 (SEQ ID NO: 16). As detailed in Table 4, additional oligonucleotides based on this oligonucleotide were designed to confirm and extend the findings described above.

Oligonucleotides ISIS Nos. 14320 (SEQ ID NO: 27) and 14321 (SEQ ID NO: 28) are 2'-deoxy-phosphorothioate sense strand and scrambled controls for ISIS 12539 (SEQ ID NO: 16), respectively. ISIS Nos. 15346 and 15347 are "gapmers" corresponding to ISIS 12539; both have 2'-methoxyethoxy "wings" (having phosphorothioate linkages in the case of ISIS 15346 and phosphodiester linkages in the case of ISIS 15347) and a central 2'-deoxy "gap" designed to support RNaseH activity on the target mRNA molecule. Similarly, ISIS Nos. 15348 to 15350 are "wingmers" corresponding to ISIS 12539 and have a 5' or 3' 2'-methoxyethoxy RNaseH-refractory "wing" and a 3' or 5' (respectively) 2'-deoxy "wing" designed to support RNaseH activity on the target JNK1 mRNA.

The chemically modified derivatives of ISIS 12539 (SEQ ID NO: 16) were tested in the Northern assay described herein at concentrations of 100 and 400 nM, and the data (Table 5) indicate the following results. At 400 nM, relative to the 2'-unmodified oligonucleotide ISIS 12539, both "gapmers" (ISIS Nos. 15346 and 15347) effected inhibition of JNK1 mRNA expression up to at least about 88% inhibition. Similarly, the four "wingmers" (ISIS Nos. 15348 to 15351) effected inhibition of JNK1 expression of up to at least about 60 to 70% inhibition.

TABLE 4

Chemically Modified JNK1 Oligonucleotides

| ISIS NO. | NUCLEOTIDE SEQUENCE (5' -> 3') AND CHEMICAL MODIFICATIONS* | SEQ ID NO: | COMMENTS |
|---|---|---|---|
| 12539 | $C^sT^sC^sT^sC^sT^sG^sT^sA^sG^sG^sC^sC^sC^sG^sC^sT^sT^sG^sG$ | 16 | active |
| 14320 | $C^sC^sA^sA^sG^sC^sG^sG^sG^sC^sC^sT^sA^sC^sA^sG^sA^sG^sA^sG$ | 27 | 12539 sense control |
| 14321 | $C^sT^sT^sT^sC^sC^sG^sT^sT^sG^sG^sA^sC^sC^sC^sC^sT^sG^sG^sG$ | 28 | scrambled control |
| 15345 | $C^sT^sC^sT^sC^sT^sG^sT^sA^sG^sG^sC^sC^sC^sG^sC^sT^sT^sG^sG$ | 16 | fully 2'-methoxyethoxy |
| 15346 | $C^sT^sC^sT^sC^sT^sG^sT^sA^sG^sG^sC^sC^sC^sG^sC^sT^sT^sG^sG$ | 16 | "gapmer" |
| 15347 | $C^oT^oC^oT^oC^sT^sG^sT^sA^sG^sG^sC^sC^sC^sG^oC^oT^oT^oG^oG$ | 16 | "gapmer" |
| 15348 | $C^sT^sC^sT^sC^sT^sG^sT^sA^sG^sG^sC^sC^sC^sG^sC^sT^sT^sG^sG$ | 16 | "wingmer" |
| 15349 | $C^sT^sC^sT^sC^sT^sG^sT^sA^sG^sG^sC^sC^sC^sG^sC^sT^sT^sG^sG$ | 16 | "wingmer" |
| 15351 | $C^oT^oC^oT^oC^oT^oG^oT^oA^sG^sG^sC^sC^sC^sG^sC^sT^sT^sG^sG$ | 16 | "wingmer" |
| 15350 | $C^sT^sC^sT^sC^sT^sG^sT^sA^sG^oG^oC^oC^oC^oG^oC^oT^oT^oG^oG$ | 16 | "wingmer" |

Emboldened residues, 2'-methoxyethoxy- residues (others are 2'-deoxy-) including "C" residues, 5-methyl-cytosines; "*o*", phosphodiester linkage; "*s*", phosphorothioate linkage.

TABLE 5

Activity of Chemically Modified JNK1 Antisense Oligonucleotides

| ISIS # | SEQ ID NO: | Oligonucleotide Description* | Dose | Normalized % Control |
|---|---|---|---|---|
| control | — | No oligonucleotide (LIPOFECTIN ™ only) | — | 100.0 |
| 12539 | 16 | JNK1 active, fully P = S & | 100 nM | 56.4 |
| 12539 | 16 | fully 2'-deoxy | 400 nM | 26.7 |
| 15345 | 16 | fully P = S & fully 2'-MOE | 100 nM | 95.4 |
| 15345 | 16 |  | 400 nM | 89.1 |
| 15346 | 16 | gapmer: P = S, 2'-MOE wings; | 100 nM | 22.6 |
| 15346 | 16 | P = S, 2'-deoxy core | 400 nM | 11.0 |
| 15347 | 16 | gapmer: P = O, 2'-MOE wings; | 100 nM | 27.1 |
| 15347 | 16 | P = S, 2-deoxy core | 400 nM | 11.7 |
| 15348 | 16 | wingmer: fully P = S; | 100 nM | 30.4 |
| 15348 | 16 | 5' 2'-MOE; 3' 2-deoxy | 400 nM | 32.9 |
| 15349 | 16 | wingmer: fully P = S; | 100 nM | 42.5 |
| 15349 | 16 | 5' 2-deoxy; 3' 2'-MOE | 400 nM | 35.5 |
| 15351 | 16 | wingmer: 5' P = O 2'-MOE; | 100 nM | 45.1 |
| 15351 | 16 | 3' P = S & 2-deoxy | 400 nM | 39.8 |
| 15350 | 16 | wingmer: 5' P = S & 2'- | 100 nM | 71.1 |
| 15350 | 16 | deoxy; 3' P = O & 2'-MOE | 400 nM | 41.3 |

*Abbreviations: P = O phosphodiester linkage; P = S, phosphorothioate linkage; MOE, methoxyethoxy-.

E. Dose- and sequence-dependent response to JNK1 oligonucleotides

In order to demonstrate a dose-dependent response to ISIS 12539 (SEQ ID NO: 16), different concentrations (i.e., 50, 100, 200 and 400 nM) of ISIS 12539 were tested for their effect on JNK1 mRNA levels in A549 cells (Table 6). In addition, two control oligonucleotides (ISIS 14320, SEQ ID NO: 27, sense control, and ISIS 14321, SEQ ID NO: 28, scrambled control; see also Table 4) were also applied to A549 cells in order to demonstrate the specificity of ISIS 12539. The results (Table 6) demonstrate that the response of A549 cells to ISIS 12539 is dependent on dose in an approximately linear fashion. In contrast, neither of the control oligonucleotides effect any consistent response on JNK1 mRNA levels.

F. Western Assays

In order to assess the effect of oligonucleotides targeted to JNK1 mRNAs on JNK1 protein levels, Western assays were performed essentially as described above in Example 2, with the following exception(s) and/or modification(s). A primary antibody that specifically binds to JNK1 (catalog No. sc-474-G) was purchased from Santa Cruz Biotechnology, Inc. (Santa Cruz, Calif.; other JNK1-specific antibodies are available from StressGen Biotechnologies, Inc., Victoria, BC, Canada; and Research Diagnostics, Inc., Flanders, N.J.). In this experiment, cells were grown and treated with oligonucleotide at 300 nM for the initial 20 hours and then at 200 nM for 4 hours. At t=48 h, aliquots were removed for Northern and Western analyses, and fresh media was added to the cells. Aliquots for analysis were also taken at t=72 h. The samples from t=48 h and t=72 h were analyzed using the Northern and Western assays described above.

TABLE 6

Dose-Dependent Responses to JNK1 Antisense Oligonucleotides

| ISIS # | SEQ ID NO: | Oligonucleotide Description | Dose | Normalized % Control |
|---|---|---|---|---|
| control | — | No oligonucleotide (LIPOFECTIN ™ only) | — | 100.0 |
| 12539 | 16 | JNK1 active | 50 nM | 70.3 |
| 12539 | 16 | " | 100 nM | 51.6 |
| 12539 | 16 | " | 200 nM | 22.4 |
| 12539 | 16 | " | 400 nM | 11.1 |
| 14320 | 27 | 12539 sense control | 50 nM | 103.6 |
| 14320 | 27 | " | 100 nM | 76.3 |
| 14320 | 27 | " | 200 nM | 98.9 |
| 14320 | 27 | " | 400 nM | 97.1 |
| 14321 | 28 | 12539 scrambled control | 50 nM | 91.8 |
| 14321 | 28 | " | 100 nM | 94.1 |
| 14321 | 28 | " | 200 nM | 100.2 |
| 14321 | 28 | " | 400 nM | 79.2 |

The data (Table 7) indicate the following results. In this assay, at t=48 h, oligonucleotides showing a level of mRNA % inhibition from>about 70% to about 100% include ISIS Nos. 12539 (phosphorothioate linkages), 15346 and 15347 ("gapmers"), and 15348 and 15351 (5' "wingmers") (SEQ ID NO: 16). Oligonucleotides showing levels of mRNA inhibition of from≧about 90% to about 100% of JNK1 mRNAs in this assay include ISIS Nos. 12539, 15345 AND 15346 (SEQ ID NO: 16). The oligonucleotides tested showed approximately parallel levels of JNK1 protein inhibition; ISIS Nos. 12539, 15346–15348 and 15351 effected levels of protein inhibition≧about 40%, and ISIS Nos. 12539, 15346 and 15347 effected levels of protein inhibition≧about 55%.

At t=72 h, oligonucleotides showing a level of mRNA % inhibition from>about 70% to about 100% include ISIS Nos. 12539 (phosphorothioate linkages), 15346 and 15347 ("gapmers"), and 15348 (5' "wingmers") (SEQ ID NO: 16). Oligonucleotides showing levels of mRNA inhibition of from≧about 90% to about 100% of JNK1 mRNAs at this point in the assay include ISIS Nos. 12539 and 15346 (SEQ ID NO: 16). Overall, the oligonucleotides tested showed higher levels of JNK1 protein inhibition at this point in the assay. With the exception of the fully 2'-methoxyethoxy-modified ISIS 15345, all of the oligonucleotides in Table 7 effect≧about 40% protein inhibition. ISIS Nos. 12539, 15346–15348 and 15351 effected levels of protein inhibition≧about 60%, and ISIS Nos. 12539, 15346 and 15347 effected levels of protein inhibition≧about 70%.

TABLE 7

Modulation of JNK1 mRNA and JNK1 Protein Levels by Modified JNK1 Antisense Oligonucleotides

| ISIS # | SEQ ID NO: | RNA % Control | RNA % Inhibition | Protein % Control | Protein % Inhibition |
|---|---|---|---|---|---|
| | | t = 48 h | | | |
| control | — | 100.0 | 0.0 | 100.0 | 0.0 |
| 12539 | 16 | 6.7 | 93.3 | 44.3 | 55.7 |
| 15345 | 16 | 70.3 | 29.7 | 105.0 | (0.0) |
| 15346 | 16 | 4.3 | 95.7 | 42.7 | 57.3 |
| 15347 | 16 | 7.9 | 92.1 | 38.8 | 61.2 |
| 15348 | 16 | 24.3 | 75.7 | 58.3 | 41.7 |
| 15349 | 16 | 63.1 | 36.9 | 69.5 | 30.5 |
| 15350 | 16 | 49.2 | 50.8 | 71.7 | 28.3 |
| 15351 | 16 | 26.9 | 73.1 | 52.4 | 47.6 |

TABLE 7-continued

Modulation of JNK1 mRNA and JNK1 Protein Levels by Modified JNK1 Antisense Oligonucleotides

| ISIS # | SEQ ID NO: | RNA % Control | RNA % Inhibition | Protein % Control | Protein % Inhibition |
|---|---|---|---|---|---|
| | | | t = 72 h | | |
| control | 16 | 100.0 | 0.0 | 100.0 | 0.0 |
| 12539 | 16 | 11.7 | 88.3 | 29.2 | 70.8 |
| 15345 | 16 | 187.4 | (0.0) | 87.8 | 12.2 |
| 15346 | 16 | 10.6 | 89.4 | 25.7 | 74.3 |
| 15347 | 16 | 8.2 | 81.8 | 28.4 | 71.6 |
| 15348 | 16 | 28.0 | 72.0 | 41.7 | 58.3 |
| 15349 | 16 | 52.0 | 48.0 | 56.5 | 43.5 |
| 15350 | 16 | 54.4 | 45.6 | 58.4 | 41.6 |
| 15351 | 16 | 46.1 | 53.9 | 37.0 | 63.0 |

G. Oligonucleotides specific for JNK1 isoforms

Subsequent to the initial descriptions of JNK1 (Derijard et al., *Cell*, 1994, 76, 1025), cDNAs encoding related isoforms of JNK1 were cloned and their nucleotide sequences determined (Gupta et al., *EMBO Journal*, 1996, 15, 2760). In addition to JNK1-α1 (GenBank accession No. L26318, locus name "HUMJNK1"), which encodes a polypeptide having an amino acid sequence identical to that of JNK1, the additional isoforms include JNK1-α2 (GenBank accession No. U34822, locus name "HSU34822"), JNK1-β1 (GenBank accession No. U35004, locus name "HSU35004") and JNK1-β2 (GenBank accession No. U35005, locus name "HSU35005"). The four isoforms of JNK1, which probably arise from alternative mRNA splicing, may each interact with different transcription factors or sets of transcription factors (Gupta et al., *EMBO Journal*, 1996, 15, 2760). As detailed below, the oligonucleotides of the invention are specific for certain members or sets of these isoforms of JNK1.

In the ORFs of mRNAs encoding JNK1/JNK1-α1 and JNK1-α2, nucleotides (nt) 631–665 of JNK1/JNK1-α1 (Genbank accession No. L26318) and nt 625–659 of JNK1-α2 (Genbank accession No. U34822) have the sequence shown below as SEQ ID NO: 63, whereas, in the ORFs of mRNAs encoding JNK1-β1 and JNK1-β2, nt 631–665 of JNK1-β1 (GenBank accession No. U35004) and nt 626–660 of JNK1-β2 (GenBank accession No. U35005) have the sequence shown below as SEQ ID NO: 64. For purposes of illustration, SEQ ID NOS: 63 and 64 are shown aligned with each other (vertical marks, "|," indicate bases that are identical in both sequences):

```
5'-AACGTGGATTTATGGTCTGTGGGGTGCATTATGGG    SEQ ID NO: 63
   ||||| ||  | ||||| || |||||||| |||||
5'-AACGTTGACATTTGGTCAGTTGGGTGCATCATGGG    SEQ ID NO: 64
```

Due to this divergence between the a and b JNK1 isoforms, antisense oligonucleotides derived from the reverse complement of SEQ ID NO: 63 (i.e., SEQ ID NO: 65, see below) can be used to modulate the expression of JNK1/JNK1-α1 and JNK1-α2 without significantly effecting the expression of JNK1-β1 and JNK1-β2. In like fashion, antisense oligonucleotides derived from the reverse complement of SEQ ID NO: 64 (i.e., SEQ ID NO: 66, see below) can be selected and used to modulate the expression of JNK1-β1 and JNK1-β2 without significantly effecting the expression of JNK1/JNK1-α1 and JNK1-α2. As an example, an oligonucleotide having a sequence derived from SEQ ID NO: 65 but not to SEQ ID NO: 66 is specifically hybridizable to mRNAs encoding JNK1/JNK1-α1 and JNK1-α2 but not to those encoding JNK1-β1 and JNK1-β2:

```
5'-CCCATAATGCACCCCACAGACCATAAATCCACGTT    SEQ ID NO: 65
   ||||| |||||||||| || |||| |  | || |||||
5'-CCCATGATGCACCCAACTGACCAAATGTCAACGTT    SEQ ID NO: 66
```

As a further example, in the ORFs of mRNAs encoding JNK1/JNK1-α1 and JNK1-α2, nt 668–711 of JNK1/JNK1-α1 (Genbank accession No. L26318) and nt 662–705 of JNK1-α2 (Genbank accession No. U34822) have the sequence shown below as SEQ ID NO: 67, whereas, in the ORFs of mRNAs encoding JNK1-β1 and JNK1-β2, nt 668–711 of JNK1-β1 (GenBank accession No. U35004) and nt 663–706 of JNK1-β2 (GenBank accession No. U35005) have the sequence shown below as SEQ ID NO: 68. For purposes of illustration, SEQ ID NOS: 67 and 68 are shown aligned with each other as follows:

```
5'-AAATGGTTTGCCACAAAATCCTCTTTCCAGGAAGGGACTATATT    SEQ ID NO: 67
   ||||| |                |  | || ||||| |   ||    |||||
5'-AAATGATCAAAGGTGGTGTTTTGTTCCCAGGTACAGATCATATT    SEQ ID NO: 68
```

Due to this divergence between the a and b JNK1 isoforms, antisense oligonucleotides derived from the reverse complement of SEQ ID NO: 67 (i.e., SEQ ID NO: 69, see below) are specifically hybridizable to mRNAs encoding, and may be selected and used to modulate the expression of, JNK1/JNK1-α1 and JNK1-α2 without significantly effecting the expression of JNK1-β1 and JNK1-β2. In like fashion, antisense oligonucleotides derived from the reverse complement of SEQ ID NO: 68 (i.e., SEQ ID NO: 70, see below) are specifically hybridizable to mRNAs encoding, and may be selected and used to modulate the expression of, can be selected and used to modulate the expression of JNK1-β1 and JNK1-β2 without significantly effecting the expression of JNK1/JNK1-α1 and JNK1-α2:

```
5'-AATATAGTCCCTTCCTGGAAAGAGGATTTTGTGGCAAACCATTT  SEQ ID NO: 69
   |||||  ||  |  ||||| || |  |           | |||||
5'-AATATGATCTGTACCTGGGAACAAAACACCACCTTTGATCATTT  SEQ ID NO: 70
```

In the case of the carboxyl terminal portion of the JNK1 isoforms, JNK1/JNK1-α1 shares identity with JNK1-β1; similarly, JNK1-α2 and JNK1-β2 have identical carboxy terminal portions. The substantial differences in the amino acid sequences of these isoforms (5 amino acids in JNK1/JNK1-α1 and JNK1-β1 are replaced with 48 amino acids in JNK1-α2 and JNK1-β2) result from a slight difference in nucleotide sequence that shifts the reading frame. Specifically, in the ORFs of mRNAs encoding JNK1/JNK1-α1 and JNK1-β1, nt 1144–1175 of JNK1/JNK1-α1 (Genbank accession No. L26318) and JNK1-β1 (Genbank accession No. U35004) have the sequence shown below as SEQ ID NO: 71, whereas, in the ORFs of mRNAs encoding JNK1-α2 and JNK1-β2, nt 1138–1164 of JNK1-α2 (GenBank accession No. U34822) and nt 1139–1165 of JNK1-β2 (GenBank accession No. U35005) have the sequence shown below as SEQ ID NO: 72. For purposes of illustration, SEQ ID NOS: 71 and 72 are shown aligned with each other (dashes, "-," indicate bases that are absent in the indicated sequence, and emboldened bases indicate the stop codon for the JNK1/JNK1-α1 and JNK1-β1 ORFs):

```
5'-CCCTCTCCTTTAGCACAGGTGCAGCAGTGATC      SEQ ID NO: 71
   ||||||||||||||        ||||||||||||||||
5'-CCCTCTCCTTTAG-----GTGCAGCAGTGATC      SEQ ID NO: 72
```

Due to this divergence between the JNK1 isoforms, antisense oligonucleotides derived from the reverse complement of SEQ ID NO: 71 (i.e., SEQ ID NO: 73, see below) are specifically hybridizable to mRNAs encoding, and may be selected and used to modulate the expression of, JNK1/JNK1-α1 and JNK1-β1 without significantly effecting the expression of JNK1-α2 and JNK1-β2. In like fashion, antisense oligonucleotides derived from the reverse complement of SEQ ID NO: 72 (i.e., SEQ ID NO: 74, see below) are specifically hybridizable to mRNAs encoding, and may be selected and used to modulate the expression of, JNK1-α2 and JNK1-β2 without significantly effecting the expression of JNK1/JNK1-α1 and JNK1-β1:

```
5'-GATCACTGCTGCACCTGTGCTAAAGGAGAGGG      SEQ ID NO: 73
   ||||||||||||||        ||||||||||||||||
5'-GATCACTGCTGCAC-----CTAAAGGAGAGGG      SEQ ID NO: 74
```

In preferred embodiments, such isoform-specific oligonucleotides such as are described above are methoxyethoxy "gapmers" or "wingmers" in which the RNase H-sensitive "gap" or "wing" is positioned so as to overlap a region of nonidentity in the above antisense sequences, i.e., SEQ ID NOS: 65, 66, 69, 70, 73 and 74.

Example 4

Oligonucleotide-Mediated Inhibition of JNK2 Expression

A. JNK2 oligonucleotide sequences

Table 8 lists the nucleotide sequences of oligonucleotides designed to specifically hybridize to JNK2 mRNAs and the corresponding ISIS and SEQ ID numbers thereof. The target gene nucleotide co-ordinates and gene target region are also included. The nucleotide co-ordinates are derived from GenBank accession No. L31951, locus name "HUMJNK2" (see also FIG. 1(A) of Sluss et al., *Mol. Cel. Biol.*, 1994, 14, 8376, and Kallunki et al., *Genes & Development*, 1994, 8, 2996). The abbreviations for gene target regions are as follows: 5'-UTR, 5' untranslated region; tIR, translation initiation region; ORF, open reading frame; 3'-UTR, 3' untranslated region. The nucleotides of the oligonucleotides whose sequences are presented in Table 8 are connected by phosphorothioate linkages and are unmodified at the 2' position (i.e., 2-deoxy). It should be noted that the oligonucleotide target co-ordinate positions and gene target regions may vary within mRNAs encoding related isoforms of JNK2 (see subsection G, below).

In addition to hybridizing to human JNK2 mRNAs, the full oligonucleotide sequence of ISIS No. 12562 (SEQ ID NO: 33) hybridizes to the ORF of mRNAs from Rattus norvegicus that encode a stress-activated protein kinase named "p54α2" (Kyriakis et al., *Nature*, 1994, 369, 156). Specifically, ISIS 12562 (SEQ ID NO: 33) hybridizes to bases 649–668 of GenBank accession No. L27112, locus name "RATSAPKB." This oligonucleotide is thus a preferred embodiment of the invention for investigating the role of the p54α2 protein kinase in rat in vitro, i.e., in cultured cells or tissues derived from whole animals, or in vivo.

B. JNK2-specific probes

In initial screenings of a set of oligonucleotides derived from the JNK2 sequence (Table 9) for biological activity, a cDNA clone of JNK2 (Kallunki et al., *Genes & Development*, 1994, 8, 2996) was radiolabeled and used as a JNK2-specific probe in Northern blots. Alternatively, however, one or more of the oligonucleotides of Table 8 is detectably labeled and used as a JNK2-specific probe.

C. Activities of JNK2 oligonucleotides

The data from screening a set of JNK2-specific phosphorothioate oligonucleotides (Table 9) indicate the following results. Oligonucleotides showing activity in this assay, as reflected by levels of inhibition from ≧ about 50% to about 100% of JNK2 mRNA levels, include ISIS Nos. 12558, 12559, 12560, 12563, 12564, 12565, 12566, 12567, 12568, 12569 and 12570 (SEQ ID NOS: 29, 30, 31, 34, 35, 36, 37, 38, 39, 40 and 41, respectively). These oligonucleotides are thus preferred embodiments of the invention for modulating JNK2 expression. Oligonucleotides showing levels of inhibition of from ≧ about 80% to about 100% of JNK2 mRNAs in this assay, include ISIS Nos. 12558, 12560, 12565, 12567, 12568 and 12569 (SEQ ID NOS: 29, 31, 36, 38, 39 and 40, respectively). These oligonucleotides are thus more preferred embodiments of the invention for modulating JNK2 expression.

The time course of inhibition of JNK2 mRNA expression by ISIS 12560 (SEQ ID NO: 31) is shown in Table 10. Following the 4 hour treatment with ISIS 12560, the level of inhibition of JNK2 was greater than or equal to about 80% for at least about 12 hours and greater than or equal to about 60% up to at least about t=48 h.

TABLE 8

Nucleotide Sequences of JNK2 Oligonucleotides

| ISIS NO. | NUCLEOTIDE SEQUENCE (5' -> 3') | SEQ ID NO: | TARGET GENE NUCLEOTIDE CO-ORDINATES | GENE TARGET REGION |
|---|---|---|---|---|
| 12558 | GTT—TCA—GAT—CCC—TCG—CCC—GC | 29 | 0003–0022 | 5'-UTR |
| 12559 | TGC—AGC—ACA—AAC—AAT—CCC—TT | 30 | 0168–0187 | ORF |
| 12560 | GTC—CGG—GCC—AGG—CCA—AAG—TC | 31 | 0563–0582 | ORF |
| 12561 | CAG—GAT—GAC—TTC—GGG—CGC—CC | 32 | 0633–0652 | ORF |
| 12562 | GCT—CTC—CCA—TGA—TGC—AAC—CC | 33 | 0691–0710 | ORF |
| 12563 | ATG—GGT—GAC—GCA—GAG—CTT—CG | 34 | 0997–1016 | ORF |
| 12564 | CTG—CTG—CAT—CTG—AAG—GCT—GA | 35 | 1180–1199 | ORF |
| 12565 | TGA—GAA—GGA—GTG—GCG—TTG—CT | 36 | 1205–1224 | ORF |
| 12566 | TGC—TGT—CTG—TGT—CTG—AGG—CC | 37 | 1273–1292 | ORF |
| 12567 | GGT—CCC—GTC—GAG—GCA—TCA—AG | 38 | 1295–1314 | ORF |
| 12568 | CAT—TTC—AGG—CCC—ACG—GAG—GT | 39 | 1376–1395 | 3'-UTR |
| 12569 | GGT—CTG—AAT—AGG—GCA—AGG—CA | 40 | 1547–1566 | 3'-UTR |
| 12570 | GGG—CAA—GTC—CAA—GCA—AGC—AT | 41 | 1669–1688 | 3'-UTR |

TABLE 9

Activities of JNK2 Oligonucleotides

| ISIS NO. | SEQ ID NO: | GENE TARGET REGION | % EXPRESSION | % INHIBITION |
|---|---|---|---|---|
| 12558 | 29 | 5'-UTR | 15% | 85% |
| 12559 | 30 | ORF | 28% | 72% |
| 12560 | 31 | ORF | 11% | 89% |
| 12561 | 32 | ORF | 60% | 40% |
| 12562 | 33 | ORF | 89% | 11% |
| 12563 | 34 | ORF | 22% | 78% |
| 12564 | 35 | ORF | 28% | 72% |
| 12565 | 36 | ORF | 19% | 81% |
| 12566 | 37 | ORF | 42% | 58% |
| 12567 | 38 | ORF | 18% | 82% |
| 12568 | 39 | 3'-UTR | 20% | 80% |
| 12569 | 40 | 3'-UTR | 13% | 87% |
| 12570 | 41 | 3'-UTR | 24% | 76% |

TABLE 10

Time Course of Response to JNK2 Antisense Oligonucleotides (ASOs)

| ISIS # | SEQ ID NO: | ASO Description | Time | Normalized % Control | % Inhibition |
|---|---|---|---|---|---|
| control | — | (LIPOFECTIN ™ only) | 0 h | 100.0 | 0.0 |
| control | — | " | 4 h | 100.0 | 0.0 |
| control | — | " | 12 h | 100.0 | 0.0 |
| control | — | " | 48 h | 100.0 | 0.0 |
| control | — | " | 72 h | 100.0 | 0.0 |
| 12560 | 31 | JNK2 active | 0 h | 20.2 | 79.8 |
| 12560 | 31 | " | 4 h | 11.1 | 88.9 |
| 12560 | 31 | " | 12 h | 21.8 | 78.2 |
| 12560 | 31 | " | 48 h | 42.7 | 57.3 |
| 12560 | 31 | " | 72 h | 116.8 | (0.0) |

D. Additional JNK2 oligonucleotides

The results for JNK2-specific oligonucleotides (Table 9) indicate that one of the most active phosphorothioate oligonucleotides for modulating JNK2 expression is ISIS 12560 (SEQ ID NO: 31). As detailed in Table 11, additional oligonucleotides based on this oligonucleotide were designed to confirm and extend the findings described above.

Oligonucleotides ISIS Nos. 14318 (SEQ ID NO: 42) and 14319 (SEQ ID NO: 43) are 2'-deoxy-phosphorothioate sense strand and scrambled controls for ISIS 12560 (SEQ ID NO: 31), respectively. ISIS Nos. 15353 and 15354 are "gapmers" corresponding to ISIS 12560; both have 2'-methoxyethoxy "wings" (having phosphorothioate linkages in the case of ISIS 15353 and phosphodiester linkages in the case of ISIS 15354) and a central 2'-deoxy "gap" designed to support RNaseH activity on the target mRNA molecule. Similarly, ISIS Nos. 15355 to 15358 are "wingmers" corresponding to ISIS 12560 and have a 5' or 3' 2'-methoxyethoxy RNaseH-refractory "wing" and a 3' or 5' (respectively) 2-deoxy "wing" designed to support RNaseH activity on the target JNK2 mRNA.

The chemically modified derivatives of ISIS 12560 (SEQ ID NO: 31) were tested in the Northern assay described herein at concentrations of 100 and 400 nM, and the data (Table 12) indicate the following results. At 400 nM, relative to the 2'-unmodified oligonucleotide ISIS 12560, both "gapmers" (ISIS Nos. 15353 and 15354) effected inhibition of JNK2 mRNA expression up to at least about 80% inhibition. Similarly, the four "wingmers" (ISIS Nos. 15355 to 15358) effected inhibition of JNK2 expression of up to at least about 70 to 90% inhibition.

E. Dose- and sequence-dependent response to JNK2 oligonucleotides

In order to demonstrate a dose-dependent response to ISIS 12560 (SEQ ID NO: 31), different concentrations (i.e., 50, 100, 200 and 400 nM) of ISIS 12560 were tested for their effect on JNK2 mRNA levels in A549 cells (Table 13). In addition, two control oligonucleotides (ISIS 14318, SEQ ID NO: 42, sense control, and ISIS 14319, SEQ ID NO: 43, scrambled control; see also Table 11) were also applied to A549 cells in order to demonstrate the specificity of ISIS 12560. The results (Table 12) demonstrate that the response of A549 cells to ISIS 12539 is dependent on dose in an approximately linear fashion. In contrast, neither of the control oligonucleotides effect any consistent response on JNK2 mRNA levels.

TABLE 11

Chemically Modified JNK2 Oligonucleotides

| ISIS NO. | NUCLEOTIDE SEQUENCE (5' -> 3') AND CHEMICAL MODIFICATIONS* | SEQ ID NO: | COMMENTS |
|---|---|---|---|
| 12560 | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | active |
| 14318 | G$^S$A$^S$C$^S$T$^S$T$^S$T$^S$G$^S$G$^S$C$^S$C$^S$T$^S$G$^S$G$^S$C$^S$C$^S$C$^S$G$^S$G$^S$A$^S$C | 42 | 12560 sense control |
| 14319 | G$^S$T$^S$G$^S$C$^S$G$^S$C$^S$G$^S$C$^S$G$^S$A$^S$G$^S$C$^S$C$^S$C$^S$G$^S$A$^S$A$^S$A$^S$T$^S$C | 43 | scrambled control |
| 15352 | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | fully 2'-methoxyethoxy |
| 15353 | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | "gapmer" |
| 15354 | G$^O$T$^O$C$^O$C$^O$G$^S$G$^S$G$^S$C$^S$C$^S$A$^S$G$^S$G$^S$C$^S$C$^S$A$^O$A$^O$A$^O$G$^O$T$^O$C | 31 | "gapmer" |
| 15355 | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | "wingmer" |
| 15356 | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | "wingmer" |
| 15358 | G$^O$T$^O$C$^O$C$^O$G$^O$G$^O$G$^O$C$^O$C$^O$A$^O$G$^S$G$^S$C$^S$C$^S$A$^S$A$^S$A$^S$G$^S$T$^S$C | 31 | "wingmer" |
| 15357 | G$^S$T$^S$C$^S$C$^S$G$^S$G$^S$G$^S$C$^S$C$^S$A$^O$G$^O$G$^O$C$^O$C$^O$A$^O$A$^O$A$^O$G$^O$T$^O$C | 31 | "wingmer" |

*Emboldened residues, 2'-methoxyethoxy- residues (others are 2'-deoxy-) including "C" residues, 5-methyl-cytosines; "$^O$", phosphodiester linkage; "$^S$", phosphorothioate linkage.

TABLE 12

Activity of Chemically Modified JNK2 Antisense Oligonucleotides

| ISIS # | SEQ ID NO: | Oligonucleotide Description | Dose | Normalized % Control |
|---|---|---|---|---|
| control | — | No oligonucleotide (LIPOFECTIN ™ only) | — | 100.0 |
| 12560 | 31 | JNK2 active, fully P = S & | 100 nM | 62.1 |
| 12560 | 31 | fully 2-deoxy | 400 nM | 31.4 |
| 15352 | 31 | fully P = S & fully 2'-MOE | 100 nM | 132.4 |
| 15352 | 31 |  | 400 nM | 158.4 |
| 15353 | 31 | gapmer: P = S, 2'-MOE wings; | 100 nM | 56.7 |
| 15353 | 31 | P = S, 2-deoxy core | 400 nM | 21.2 |
| 15354 | 31 | gapmer: P = O, 2'-MOE wings; | 100 nM | 38.3 |
| 15354 | 31 | P = S, 2-deoxy core | 400 nM | 17.1 |
| 15355 | 31 | wingmer: fully P = S; | 100 nM | 61.3 |
| 15355 | 31 | 5' 2'-MOE; 3' 2-deoxy | 400 nM | 29.1 |
| 15356 | 31 | wingmer: fully P = S; | 100 nM | 38.6 |
| 15356 | 31 | 5' 2-deoxy; 3' 2'-MOE | 400 nM | 11.0 |
| 15358 | 31 | wingmer: 5' P = O & 2'-MOE; | 100 nM | 47.4 |
| 15358 | 31 | 3' P = S & 2-deoxy | 400 nM | 29.4 |
| 15357 | 31 | wingmer: 5' P = S & 2'- | 100 nM | 42.8 |
| 15357 | 31 | deoxy; 3' P = O & 2'-MOE | 400 nM | 13.7 |

TABLE 13

Dose-Dependent Responses to JNK2 Antisense Oligonucleotides

| ISIS # | SEQ ID NO: | Oligonucleotide Description | Dose | Normalized % Control |
|---|---|---|---|---|
| control | — | No oligonucleotide (LIPOFECTIN™ only) | — | 100.0 |
| 12560 | 31 | JNK2 active | 50 nM | 68.1 |
| 12560 | 31 | " | 100 nM | 50.0 |
| 12560 | 31 | " | 200 nM | 25.1 |
| 12560 | 31 | " | 400 nM | 14.2 |
| 14318 | 42 | 12560 sense control | 50 nM | 87.1 |
| 14318 | 42 | " | 100 nM | 89.8 |
| 14318 | 42 | " | 200 nM | 92.1 |
| 14318 | 42 | " | 400 nM | 99.6 |
| 14319 | 43 | 12560 scrambled control | 50 nM | 90.4 |
| 14319 | 43 | " | 100 nM | 93.7 |
| 14319 | 43 | " | 200 nM | 110.2 |
| 14319 | 43 | " | 400 nM | 100.0 |

F. Western Assays

In order to assess the effect of oligonucleotides targeted to JNK2 mRNAs on JNK2 protein levels, Western assays are performed essentially as described above in Examples 2 and 3. A primary antibody that specifically binds to JNK2 is purchased from, for example, Santa Cruz Biotechnology, Inc., Santa Cruz, Calif.; Upstate Biotechnology, Inc., Lake Placid, N.Y.; StressGen Biotechnologies, Inc., Victoria, BC, Canada; or Research Diagnostics, Inc., Flanders, N.J.

G. Oligonucleotides specific for JNK2 isoforms

Subsequent to the initial descriptions of JNK2 (Sluss et al., *Mol. Cel. Biol.*, 1994, 14, 8376; Kallunki et al., *Genes & Development*, 1994, 8, 2996; GenBank accession No. HSU09759, locus name "U09759"), cDNAs encoding related isoforms of JNK2 were cloned and their nucleotide sequences determined (Gupta et al., *EMBO Journal*, 1996, 15, 2760). In addition to JNK2-α2 (GenBank accession No. L31951, locus name "HUMJNK2"), which encodes a polypeptide having an amino acid sequence identical to that of JNK2, the additional isoforms include JNK2-α1 (GenBank accession No. U34821, locus name "HSU34821"), JNK2-β1 (GenBank accession No. U35002, locus name "HSU36002") and JNK2-β2 (GenBank accession No. U35003, locus name "HSU35003"). The four isoforms of JNK2, which probably arise from alternative mRNA splicing, may each interact with different transcription factors or sets of transcription factors (Gupta et al., *EMBO Journal*, 1996, 15, 2760). As detailed below, the oligonucleotides of the invention are specific for certain members or sets of these isoforms of JNK2.

In the ORFs of mRNAs encoding JNK2/JNK2-α2 and JNK2-α1, nucleotides (nt) 689–748 of JNK2/JNK2-α2 (Genbank accession No. L31951) and nt 675–734 of JNK2-α1 (Genbank accession No. U34821) have the sequence shown below as SEQ ID NO: 75, whereas, in the ORFs of mRNAs encoding JNK2-β1 and JNK2-β2, nt 653–712 of JNK2-β1 (GenBank accession No. U35002) and nt 665–724 of JNK2-β2 (GenBank accession No. U35003) have the sequence shown below as SEQ ID NO: 76. For purposes of illustration, SEQ ID NOS: 75 and 76 are shown aligned with each other (vertical marks, "|," indicate bases that are identical in both sequences):

```
5'-GTGGGTTGCATCATGGGAGAGCTGGTGAAAGGTTGTGTGATATTCCAAGGCACTGACCAT    SEQ ID NO: 75
   || || |||||||||||  |||  ||||       |   ||  | ||||  || |  ||| ||
5'-GTCGGGTGCATCATGGCAGAAATGGTCCTCCATAAAGTCCTGTTCCCGGGAAGAGACTAT   SEQ ID NO: 76
```

Due to this divergence between the a and b JNK2 isoforms, antisense oligonucleotides derived from the reverse complement of SEQ ID NO: 75 (i.e., SEQ ID NO: 77, see below) are specifically hybridizable to, and may be selected and used to modulate the expression of, JNK2/JNK2-α2 and JNK2-α1 without significantly effecting the expression of JNK1-β1 and JNK1-β2. In like fashion, antisense oligonucleotides derived from the reverse complement of SEQ ID NO: 76 (i.e., SEQ ID NO: 78, see below) are specifically hybridizable to, and may be selected and used to modulate the expression of, JNK2-β1 and JNK2-β2 without significantly effecting the expression of JNK2/JNK2-α2 and JNK2-α1. As an example, an oligonucleotide having a sequence derived from SEQ ID NO: 77 but not from SEQ ID NO: 78 is specifically hybridizable to, mRNAs encoding JNK1/JNK1-α1 and JNK1-α2 but not to those encoding JNK2-β1 and JNK2-β2:

```
5'-GATCAGCCTTCAGCACAGATGCAGCAGTAAGTAGC    SEQ ID NO: 79
   ||||||||||||||        ||||||||||||||||||||
5'-GATCAGCCTTCAG-----ATGCAGCAGTAAGTAGC     SEQ ID NO: 80
```

Due to this divergence between the JNK2 isoforms, antisense oligonucleotides derived from the reverse complement of SEQ ID NO: 79 (i.e., SEQ ID NO: 81, see below) are specifically hybridizable to, and may be selected and used to modulate the expression of, mRNAs encoding JNK2-α1 and JNK2-β1 without significantly effecting the expression of JNK2/JNK2-α2 and JNK2-β2. In like fashion, antisense oligonucleotides derived from the reverse complement of

```
5'-ATGGTCAGTGCCTTGGAATATCACACAACCTTTCACCAGCTCTCCCATGATGCAACCCAC    SEQ ID NO: 77
   || |||  |  ||  ||||  |  ||      |    ||||  ||| |||||||||| || ||
5'-ATAGTCTCTTCCCGGGAACAGGACTTTATGGAGGACCATTTCTGCCATGATGCACCCGAC   SEQ ID NO: 78
```

In the case of the carboxyl terminal portion of the JNK2 isoforms, JNK2/JNK2-α2 shares identity with JNK1-β2; similarly, JNK2-α1 and JNK2-β1 have identical carboxy terminal portions. The substantial differences in the amino acid sequences of these isoforms (5 amino acids in JNK2-α2 and JNK2-β2 are replaced with 47 amino acids in JNK2/JNK2-α2 and JNK2-β2) result from a slight difference in nucleotide sequence that shifts the reading frame. Specifically, in the ORFs of mRNAs encoding JNK2-α1 and JNK1-β1, nt 1164–1198 of JNK2-α1 (Genbank accession No. U34821) and nt 1142–1176 of JNK2-β1 (Genbank accession No. U35002) have the sequence shown below as SEQ ID NO: 79, whereas, in the ORFs of mRNAs encoding JNK2/JNK2-α2 and JNK2-β2, nt 1178–1207 of JNK2/JNK2-α2 (GenBank accession No. L31951) and nt 1154–1183 of JNK2-β2 (GenBank accession No. U35003) have the sequence shown below as SEQ ID NO: 80. For purposes of illustration, SEQ ID NOS: 79 and 80 are shown aligned with each other (dashes, "-," indicate bases that are absent in the indicated sequence, and emboldened bases indicate the stop codon for the JNK2-α1 and JNK2-β1 ORFs):

SEQ ID NO: 80 (i.e., SEQ ID NO: 82, see below) are specifically hybridizable to, and may be selected and used to modulate the expression of, mRNAs encoding JNK2/JNK2-α2 and JNK2-β2 without significantly effecting the expression of JNK2-α1 and JNK2-β1. As an example, ISIS 12564 (SEQ ID NO: 35) corresponds to SEQ ID NO: 82 but not to SEQ ID NO: 81, and is thus specifically hybridizable to, and may be used to modulate the expression of, mRNAs encoding JNK2/JNK2-α2 and JNK2-β2 but not those encoding JNK2-α1 and JNK2-β1:

```
5'-GCTACTTACTGCTGCATCTGTGCTGAAGGCTGATC        SEQ ID NO: 81
   |||||||||||||||||         |||||||||||
5'-GCTACTTACTGCTGCAT-----CTGAAGGCTGATC        SEQ ID NO: 82
        |||||||||        |||||||||||
5'-CTGCTGCAT-----CTGAAGGCTGA                  SEQ ID NO: 35
```

In preferred embodiments, such isoform-specific oligonucleotides such as are described above are methoxyethoxy "gapmers" or "wingmers" in which the RNase H-sensitive "gap" or "wing" is positioned so as to overlap a region of nonidentity in the above antisense sequences, i.e., SEQ ID NOS: 77, 78, 81 and 82.

Example 5

Oligonucleotide-Mediated Inhibition of JNK3 Expression

A. JNK3 oligonucleotide sequences

Table 14 lists the nucleotide sequences of oligonucleotides designed to specifically hybridize to JNK3 mRNAs and the corresponding ISIS and SEQ ID numbers thereof. The target gene nucleotide co-ordinates and gene target region are also included. The nucleotide co-ordinates are derived from GenBank accession No. U07620, locus name "HSU07620" see also FIG. 4(A) of Mohit et al., *Neuron*, 1994, 14, 67). The abbreviations for gene target regions are as follows: 5'-UTR, 5' untranslated region; tIR, translation initiation region; ORF, open reading frame; 3'-UTR, 3' untranslated region. It should be noted that the oligonucleotide target co-ordinate positions and gene target regions may vary within mRNAs encoding related isoforms of JNK3 (see subsection D, below).

The nucleotides of the oligonucleotides whose sequences are presented in Table 14 are connected by phosphorothioate linkages and are "gapmers." Specifically, the six nucleotides of the 3' and 5' termini are 2'-methoxyethoxy- modified and are shown emboldened in Table 14, whereas the central eight nucleotides are unmodified at the 2' position (i.e., 2-deoxy).

In addition to hybridizing to human JNK3 mRNAs, the full oligonucleotide sequences of ISIS Nos. 16692, 16693, 16703, 16704, 16705, 16707, and 16708 (SEQ ID NOS: 46, 47, 56, 57, 58, 60 and 61, respectively) specifically hybridize to mRNAs from Rattus norvegicus that encode a stress-activated protein kinase named "p54β" (Kyriakis et al., *Nature*, 1994, 369, 156; GenBank accession No. L27128, locus name "RATSAPKC." Furthermore, the full oligonucleotide sequences of 16692, 16693, 16695, 16703, 16704, 16705, 16707 and 16708 (SEQ ID NOS: 46, 47, 49, 56, 57, 58, 60 and 61, respectively) specifically hybridize to mRNAs from *Mus musculus* that encode a mitogen activated protein (MAP) kinase stress activated protein named the "p459$^{3F12}$ SAP kinase" (Martin et al., *Brain Res. Mol. Brain Res.*, 1996, 35, 47; GenBank accession No. L35236, locus name "MUSMAPK"). These oligonucleotides are thus preferred embodiments of the invention for investigating the role of the p54β and p459$^{3F12}$ SAP protein kinases in rat or mouse, respectively, in vitro, i.e., in cultured cells or tissues derived from whole animals or in vivo. The target gene nucleotide co-ordinates and gene target regions for these oligonucleotides, as defined for these GenBank entries, are detailed in Table 15.

B. JNK3-specific probes

In initial screenings of a set of oligonucleotides derived from the JNK3 sequence for biological activity, a CDNA clone of JNK3 (Derijard et al., *Cell*, 1994, 76, 1025) was radiolabeled and used as a JNK3-specific probe in Northern blots. Alternatively, however, one or more of the oligonucleotides of Table 14 is detectably labeled and used as a JNK3-specific probe.

C. Western Assays

In order to assess the effect of oligonucleotides targeted to JNK3 mRNAs on JNK3 protein levels, Western assays are performed essentially as described above in Examples 2 through 4. A primary antibody that specifically binds to JNK3 is purchased from, for example, Upstate Biotechnology, Inc. (Lake Placid, N.Y.), StressGen Biotechnologies Corp. (Victoria, BC, Canada), or New England Biolabs, Inc. (Beverly, Mass.).

TABLE 14

Nucleotide Sequences of JNK3 Oligonucleotides

| ISIS NO. | NUCLEOTIDE SEQUENCE[1] (5' -> 3') | SEQ ID NO: | TARGET GENE NUCLEOTIDE CO-ORDINATES | GENE TARGET REGION |
|---|---|---|---|---|
| 16690 | TTC—AAC—AGT—TTC—TTG—CAT—AA | 44 | 0157–0176 | 5'-UTR |
| 16691 | CTC—ATC—TAT—AGG—AAA—CGG—GT | 45 | 0182–0200 | 5'-UTR |
| 16692 | TGG—AGG—CTC—ATA—AAT—ACC—AC | 46 | 0215–0234 | tIR |
| 16693 | TAT—AAG—AAA—TGG—AGG—CTC—AT | 47 | 0224–0243 | tIR |
| 16694 | TCA—CAT—CCA—ATG—TTG—GTT—CA | 48 | 0253–0272 | ORF |
| 16695 | TTA—TCG—AAT—CCC—TGA—CAA—AA | 49 | 0281–0300 | ORF |
| 16696 | GTT—TGG—CAA—TAT—ATG—ACA—CA | 50 | 0310–0329 | ORF |
| 16697 | CTG—TCA—AGG—ACA—GCA—TCA—TA | 51 | 0467–0486 | ORF |
| 16698 | AAT—CAC—TTG—ACA—TAA—GTT—GG | 52 | 0675–0694 | ORF |
| 16699 | TAA—ATC—CCT—GTG—AAT—AAT—TC | 53 | 0774–0793 | ORF |
| 16700 | GCA—TCC—CAC—AGA—CCA—TAT—AT | 54 | 0957–0976 | ORF |
| 16702 | TGT—TCT—CTT—TCA—TCC—AAC—TG | 55 | 1358–1377 | ORF |
| 16703 | TCT—CAC—TGC—TGT—TCA—CTG—CT | 56 | 1485–1504 | tIR |
| 16704 | GGG—TCT—GGT—CGG—TGG—ACA—TG | 57 | 1542–1561 | 3'-UTR |
| 16705 | AGG—CTG—CTG—TCA—GTG—TCA—GA | 58 | 1567–1586 | 3'-UTR |
| 16706 | TCA—CCT—GCA—ACA—ACC—CAG—GG | 59 | 1604–1623 | 3'-UTR |
| 16707 | GCG—GCT—AGT—CAC—CTG—CAA—CA | 60 | 1612–1631 | 3'-UTR |
| 16708 | CGC—TGG—GTT—TCG—CAG—GCA—GG | 61 | 1631–1650 | 3'-UTR |
| 16709 | ATC—ATC—TCC—TGA—AGA—ACG—CT | 62 | 1647–1666 | 3'-UTR |

[1]Emboldened residues are 2'-methoxyethoxy- modified.

TABLE 15

Rat and Mouse Gene Target Locations of JNK3 Oligonucleotides

| ISIS NO. | SEQ ID NO: | Rat p54β NUCLEOTIDE CO-ORDINATES[1] | GENE TARGET REGION | Mouse p459[3F12] NUCLEOTIDE CO-ORDINATES[2] | GENE TARGET REGION |
|---|---|---|---|---|---|
| 16692 | 46 | 0213–0232 | 5'-UTR | 0301–0320 | tlR |
| 16693 | 47 | 0222–0241 | 5'-UTR | 0310–0329 | tlR |
| 16695 | 49 | — | — | 0367–0386 | ORF |
| 16703 | 56 | 1506–1525 | ORF | 1571–1590 | tTR |
| 16704 | 57 | 1563–1582 | ORF | 1628–1647 | 3'-UTR |
| 16705 | 58 | 1588–1607 | ORF | 1653–1672 | 3'-UTR |
| 16707 | 60 | 1633–1652 | tTR | 1698–1717 | 3'-UTR |
| 16708 | 61 | 1652–1671 | 3'-UTR | 1717–1736 | 3'-UTR |

[1]Co-ordinates from Genbank Accession No. L27128, locus name "RATSAPKC."
[2]Co-ordinates from Genbank Accession No. L35236, locus name "MUSMAPK."

D. Oligonucleotides specific for JNX3 isoforms

Two isoforms of JNK3 have been described. JNK3-α1 was initially cloned and named "p49[3F12] kinase" by Mohit et al. (*Neuron*, 1995, 14, 67). Subsequently, two cDNAs encoding related isoforms of JNK3 were cloned and their nucleotide sequences determined (Gupta et al., *EMBO Journal*, 1996, 15, 2760). The isoforms are named JNK3-α1 (GenBank accession No. U34820, locus name "HSU34820") and JNK3-α2 (GenBank accession No. U34819, locus name "HSU34819") herein. The two isoforms of JNK3, which probably arise from alternative mRNA splicing, may each interact with different transcription factors or sets of transcription factors (Gupta et al., *EMBLO Journal*, 1996, 15, 2760). As detailed below, certain oligonucleotides of the invention are specific for each of these isoforms of JNK3.

JNK3-α1 and JNK-α2 differ at their carboxyl terminal portions. The substantial differences in the amino acid sequences of these isoforms (5 amino acids in JNK3-α1 are replaced with 47 amino acids in JNK3-α2) result from a slight difference in nucleotide sequence that shifts the reading frame. Specifically, in the ORF of mRNAs encoding JNK3-α1, nucleotides (nt) 1325–1362 of JNK3-α1 (Genbank accession No. U34820) have the sequence shown below as SEQ ID NO: 83, whereas, in the ORF of mRNAs encoding JNK3-α2, nt 1301–1333 of JNK3-α2 (GenBank accession No. U34819) have the sequence shown below as SEQ ID NO: 84. For purposes of illustration, SEQ ID NOS: 83 and 202 are shown aligned with each other (vertical marks, "|," indicate bases that are identical in both sequences; dashes, "-," indicate bases that are absent in the indicated sequence; and emboldened bases indicate the stop codon for the JNK3-α1 ORF):

```
5'-GGACAGCCTTCTCCTTCAGCACAGGTGCAGCAGTGAAC   SEQ ID NO: 83
   ||||||||||||||||||     ||||||||||||||
5'-GGACAGCCTTCTCCTTCAG-----GTGCAGCAGTGAAC   SEQ ID NO: 84
```

Due to this divergence between the JNK3 isoforms, antisense oligonucleotides derived from the reverse complement of SEQ ID NO: 83 (i.e., SEQ ID NO: 85, see below) are specifically hybridizable to mRNAs encoding, and may be selected and used to modulate the expression of JNK3-α1 without significantly effecting the expression of JNK3-α2. In like fashion, antisense oligonucleotides derived from the reverse complement of SEQ ID NO: 84 (i.e., SEQ ID NO: 86, see below) are specifically hybridizable to mRNAs encoding, and may be selected and used to modulate the expression of JNK3-α2 without significantly effecting the expression of JNK3-α1:

```
5'-GTTCACTGCTGCACCTGTGCTGAAGGAGAAGGCTGTCC   SEQ ID NO: 85
   ||||||||||||||    ||||||||||||||||||||
5'-GTTCACTGCTGCAC-----CTGAAGGAGAAGGCTGTCC   SEQ ID NO: 86
```

In preferred embodiments, such isoform-specific oligonucleotides such as are described above are methoxyethoxy "gapmers" or "wingmers" in which the RNase H-sensitive "gap" or "wing" is positioned so as to overlap a region of nonidentity in the above antisense sequences, i.e., SEQ ID NOS: 85 and 86.

Example 6

Effect of Oligonucleotides Targeted to AP-1 Subunits on Enzymes Involved in Metastasis Patients having benign tumors, and primary malignant tumors that have been detected early in the course of their development, may often be successfully treated by the surgical removal of the benign or primary tumor. If unchecked, however, cells from malignant tumors are spread throughout a patient's body and meh the processes of invasion and metastasis. Invasion refers to the ability of cancer cells to detach from a primary site of attachment and penetrate, e.g., an underlying basement membrane. Metastasis indicates a sequence of events wherein (1) a cancer cell detaches from its extracellular matrices, (2) the detached cancer cell migrates to another portion of the patient's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.,* 1996, 275, 72).

The matrix metalloproteinases (MMPs) are a family of enzymes which have the ability to degrade components of the extracellular matrix (Birkedal-Hansen, *Current Op. Biol.,* 1995, 7, 728). Many members of the MMP family have been found to have elevated levels of activity in human tumors as well as othter disease states (Stetler-Stevenson et al., *Annu. Rev. Cell Biol.,* 1993, 9, 541; Bernhard et al., *Proc. Natl. Acad. Sci.* (U.S.A.), 1994, 91, 4293). In particular, one member of this family, matrix metalloproteinase-9 (MMP-9), is often found to be expressed only in tumors and other diseased tissues (Himelstein et al., *Invasion & Metastasis,* 1994, 14, 246). Several studies have shown that regulation of the MMP-9 gene may be controlled by the AP-1 transcription factor (Kerr et al., *Science,* 1988, 242, 1424–1427; Kerr et al., *Cell,* 1990, 61, 267; Gum et al., *J. Biol. Chem.,* 1996, 271, 10672; Hua et al., *Cancer Res.,* 1996, 56, 5279). In order to determine whether MMP-9 expression can be influenced by AP-1 modulation, the following experiments were conducted on normal human epidermal keratinocytes (NHEKs). Although NHEKs normally express no detectable MMP-9, MMP-9 can be induced by a number of stimuli, including TPA (12-O-tetradecanoylphorbol 13-acetate). ISIS 10582, an oligonucleotide targeted to c-jun, was evaluated for its ability to modulate MMP-9 expression (see pending application Ser. No. 08/837,201, filed Apr. 14, 1997, attorney docket No. ISPH-0209. The results (Table 16) demonstrate that ISIS 10582 is able to completely inhibit the expression of MMP-9 after induction with TPA.

TABLE 16

Effect of c-jun Oligonucleotide on MMP-9 Expression

| Treatment | MMP-9 |
|---|---|
| Basal | 4 |
| TPA - no oligo | 100 |
| 10582: c-jun active | 6 |
| 11562: sense control | 99 |
| 11563: scrambled control | 95 |
| 11564: mismatch control | 89 |

These results demonstrate that c-Jun is required for TPA-mediated induction of MMP-9, and indicate that oligonucleotides targeted to AP-1 subunits can inhibit the expression of MMP family members, thereby modulating the ability of cancer cells to invade other tissues and/or metastasize to other sites in a patient's body. Because JNK proteins activate AP-1 by phosphorylating the N-terminal portion of the Jun subunit thereof, modulation of one or more JNK proteins by the oligonucleotides of the present disclosure will also modulate the expression of MMP family members and limit the metastatic ability of cancer cells.

What is claimed is:

1. An antisense oligonucleotide consisting of a nucleotide sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25 or 26, wherein said antisense oligonucleotide inhibits JNK1 expression.

2. An antisense oligonucleotide consisting of a nucleotide sequence set forth in SEQ ID NO: 29, 30, 31, 32, 33, 34, 35, 36, 37, 38, 39, 40 or 41, wherein said antisense oligonucleotide inhibits JNK2 expression.

* * * * *

UNITED STATES PATENT AND TRADEMARK OFFICE
CERTIFICATE OF CORRECTION

PATENT NO. : 5,877,309
DATED : March 2, 1999
INVENTOR(S) : McKay et al.

It is certified that error appears in the above-identified patent and that said Letters Patent is hereby corrected as shown below:

Column 4,
Line 60, please delete "expressioat" and insert therefor -- expression --.

Column 9,
Line 52, please delete "10:111" and insert therefor -- 10:1111 --.

Column 12,
Line 42, please delete "846" and insert therefor -- (84%) --.

Column 23,
Line 59, please delete "opacities" and insert therefor -- opacifiers --.

Column 34,
Table 4, ISIS No. 15345, please delete
"$C^sT^sC^sT^sC^sT^sG^sT^sA^sG^sG^sC^sC^sC^sG^sC^sT^sT^sG^sG$" and insert therefor --
$C^sT^sC^sT^sC^sT^sG^sT^sA^sG^sG^sC^sC^sC^sG^sC^sT^sT^sG^sG$ --.
Table 4, ISIS No. 15346, please delete
"$C^sT^sC^sT^sC^sT^sG^sT^sA^sG^sG^sC^sC^sC^sG^sC^sT^sT^sG^sG$" and inser therefor --
$C^sT^sC^sT^sC^sT^sG^sT^sA^sG^sG^sC^sC^sC^sG^sC^sT^sT^sG^sG$ --.
Table 4, ISIS No. 15347, please delete
"$C^oT^oC^oT^oC^sT^sG^sT^sA^sG^sG^sC^sC^sC^sG^oC^oT^oT^oG^oG$" and insert therefor --
$C^oT^oC^oT^oC^sT^sG^sT^sA^sG^sG^sC^sC^sC^sG^oC^oT^oT^oG^oG$ --.
Table 4, ISIS No. 15348, please delete
"$C^sT^sC^sT^sC^sT^sG^sT^sA^sG^sG^sC^sC^sC^sG^sC^sT^sT^sG^sG$" and inset therefor --
$C^sT^sC^sT^sC^sT^sG^sT^sA^sG^sG^sC^sC^sC^sG^sC^sT^sT^sG^sG$ --.
Table 4, ISIS No. 15349, please delete
"$C^sT^sC^sT^sC^sT^sG^sT^sA^sG^sG^sC^sC^sC^sG^sC^sT^sT^sG^sG$" and insert therfor --
$C^sT^sC^sT^sC^sT^sG^sT^sA^sG^sG^sC^sC^sC^sG^sC^sT^sT^sG^sG$ --.
Table 4, ISIS No. 15351, please delete
"$C^oT^oC^oT^oC^oT^oG^oT^oA^oG^oG^sC^sC^sC^sG^sC^sT^sT^sG^sG$" an insert therefor --
$C^oT^oC^oT^oC^oT^oG^oT^oA^oG^oG^sC^sC^sC^sG^sC^sT^sT^sG^sG$ --.
Table 4, ISIS No. 15350, please delete
"$C^sT^sC^sT^sC^sT^sG^sT^sA^sG^oG^oC^oC^oC^oG^oC^oT^oT^oG^oG$" and insert therefor --
$C^sT^sC^sT^sC^sT^sG^sT^sA^sG^oG^oC^oC^oC^oG^oC^oT^oT^oG^oG$ --.

Column 35,
Line 2, please delete "C" and insert therefor -- "C" --.

Column 39,
Line 28, in SEQ ID NO. 71, please delete
"5' -CCCTCTCCTTTAGCACAGGTGCAGCAGTGATC" and insert therefor

UNITED STATES PATENT AND TRADEMARK OFFICE
CERTIFICATE OF CORRECTION

PATENT NO. : 5,877,309
DATED : March 2, 1999
INVENTOR(S) : McKay et al.

Page 2 of 4

It is certified that error appears in the above-identified patent and that said Letters Patent is hereby corrected as shown below:

Column 43,
Table 11, ISIS No. 15352, please delete
"$G^ST^SC^SC^SG^SG^SG^SC^SC^SA^SG^SG^SC^SC^SA^SA^SA^SG^ST^SC$" and insert therefor
-- $G^ST^SC^SC^SG^SG^SG^SC^SC^SA^SG^SG^SC^SC^SA^SA^SA^SG^ST^SC$ --.
Table 11, ISIS No. 15353, please delete
"$G^ST^SC^SC^SG^SG^SG^SC^SC^SA^SG^SG^SC^SC^SA^SA^SA^SG^ST^SC$" and insert therefor
-- $G^ST^SC^SC^SG^SG^SG^SC^SC^SA^SG^SG^SC^SC^SA^SA^SA^SG^ST^SC$ --.
Table 11, ISIS No. 15354, please delete
"$G^OT^OC^OC^OG^SG^SG^SC^SC^SA^SG^SG^SC^SC^SA^OA^OA^OG^OT^OC$" and insert therefor
-- $G^OT^OC^OC^OG^SG^SG^SC^SC^SA^SG^SG^SC^SC^SA^OA^OA^OG^OT^OC$ --
Table 11, ISIS No. 15355, please delete
"$G^ST^SC^SC^SG^SG^SG^SC^SC^SA^SG^SG^SC^SC^SA^SA^SA^SG^ST^SC$" and insert therefor
-- $G^ST^SC^SC^SG^SG^SG^SC^SC^SA^SG^SG^SC^SC^SA^SA^SA^SG^ST^SC$ --.
Table 11, ISIS No. 15356, please delete
"$G^ST^SC^SC^SG^SG^SG^SC^SC^SA^SG^SG^SC^SC^SA^SA^SA^SG^ST^SC$" and insert therefor
-- $G^ST^SC^SC^SG^SG^SG^SC^SC^SA^SG^SG^SC^SC^SA^SA^SA^SG^ST^SC$ --.
Table 11, ISIS No. 15358, please delete
"$G^OT^OC^OC^OG^OG^OG^OC^OC^OA^OG^SG^SC^SC^SA^SA^SA^SG^ST^SC$" and insert therefore
-- $G^OT^OC^OC^OG^OG^OG^OC^OC^OA^OG^SG^SC^SC^SA^SA^SA^SG^ST^SC$ --.
Table 11, ISIS No. 15357, please delete
"$G^ST^SC^SC^SG^SG^SG^SC^SC^SA^OG^OG^OC^OC^OA^OA^OA^OG^OT^OC$" and insert therefore
-- $G^ST^SC^SC^SG^SG^SG^SC^SC^SA^OG^OG^OC^OC^OA^OA^OA^OG^OT^OC$ --.

Column 46,
Seq. ID# 79, please delete
"5'-GATCAGCCTTCAGCACAGATGCAGCAGTAAGTAGC" and insert therefor
-- 5'-GATCAGCCTTCAGCACAGATGCAGCAGTAAGTAGC --.

Column 48,
Table 14, ISIS No. 16690, please delete "TTC-AAC-AGT-TTC-TTG-CAT-AA" and insert therefore -- TTC–AAC–AGT–TTC–TTG–CAT–AA --.
Table 14, ISIS No. 16691, please delete "CTC-ATC-TAT-AGG-AAA-CGG-GT" and insert therefor -- CTC–ATC–TAT–AGG–AAA–CGG–GT --.
Table 14, ISIS No. 16692, please delete "TGG-AGG-CTC-ATA-AAT-ACC-AC" and insert therefore -- TGG–AGG–CTC–ATA–AAT–ACC–AC --.
Table 14, ISIS No. 16693, please delete "TAT-AAG-AAA-TGG-AGG-CTC-AT" and insert therefor -- TAT–AAG–AAA–TGG–AGG–CTC–AT --.
Table 14, ISIS No. 16694, please delete "TCA-CAT-CCA-ATG-TTG-GTT-CA" and insert therefor -- TCA–CAT–CCA–ATG–TTG–GTT–CA --.

UNITED STATES PATENT AND TRADEMARK OFFICE
CERTIFICATE OF CORRECTION

PATENT NO. : 5,877,309  
DATED : March 2, 1999  
INVENTOR(S) : McKay et al.

Page 3 of 4

It is certified that error appears in the above-identified patent and that said Letters Patent is hereby corrected as shown below:

Column 48, cont'd,
Table 14, ISIS No. 16695, please delete "TTA-TCG-AAT-CCC-TGA-CAA-AA" and insert therefor -- TTA-TCG-AAT-CCC-TGA-CAA-AA --.
Table 14, ISIS No. 16696, please delete "GTT-TGG-CAA-TAT-ATG-ACA-CA" and insert therefor -- GTT-TGG-CAA-TAT-ATG-ACA-CA --.
Table 14, ISIS No. 16697, please delete " CTG-TCA-AGG-ACA-GCA-TCA-TA" and insert therefore -- CTG-TCA-AGG-ACA-GCA-TCA-TA --.
Table 14, ISIS No. 16698, please delete "AAT-CAC-TTG-ACA-TAA-GTT-GG" and insert therefor -- AAT-CAC-TTG-ACA-TAA-GTT-GG --.
Table 14, ISIS No. 16699, please delete "TAA-ATC-CCT-GTG-AAT-AAT-TC" and insert therefor -- TAA-ATC-CCT-GTG-AAT-AAT-TC --.
Table 14 ISIS No. 16700, please delete "GCA-TCC-CAC-AGA-CCA-TAT-AT" and insert therefor -- GCA-TCC-CAC-AGA-CCA-TAT-AT --.
Table 14, ISIS No. 16702, please delete "TGT-TCT-CTT-TCA-TCC-AAC-TG" and insert therefor -- TGT-TCT-CTT-TCA-TCC-AAC-TG --.
Table 14, ISIS No. 16703, please delete "TCT-CAC-TGC-TGT-TCA-CTG-CT" and insert therefor -- TCT-CAC-TGC-TGT-TCA-CTG-CT --.
Table 14, ISIS No. 16704, please delete "GGG-TCT-GGT-CGG-TGG-ACA-TG" and insert therefor -- GGG-TCT-GGT-CGG-TGG-ACA-TG --.
Table 14, ISIS No. 16705, please delete "AGG-CTG-CTG-TCA-GTG-TCA-GA" and insert therefore -- AGG-CTG-CTG-TCA-GTG-TCA-GA --.
Table 14 ISIS No. 16706, please delete "TCA-CCT-GCA-ACA-ACC-CAG-GG" and insert therefor -- TCA-CCT-GCA-ACA-ACC-CAG-GG --.
Table 14, ISIS No. 16707, please delete "GCG-GCT-AGT-CAC-CTG-CAA-CA" and insert therefor -- GCG-GCT-AGT-CAC-CTG-CAA-CA --.
Table 14, ISIS No. 16708, please delete "CGC-TGG-GTT-TCG-CAG-GCA-GG" and insert therefor -- CGC-TGG-GTT-TCG-CAG-GCA-GG --.
Table 14, ISIS No. 16709, please delete "ATC-ATC-TCC-TGA-AGA-ACG-CT" and insert therefor -- ATC-ATC-TCC-TGA-AGA-ACG-CT --.

Column 49,
Line 41, please delete "EMBLO" and insert therefore -- EMBO --.

Column 50,
SEQ ID 83, please delete "GCTACTTACT GCTGCATCTG AAGGCTGATC" and insert therefor -- GCTACTTACT GCTGCATCTG AAGGCTGATC --

UNITED STATES PATENT AND TRADEMARK OFFICE
CERTIFICATE OF CORRECTION

PATENT NO. : 5,877,309
DATED : March 2, 1999
INVENTOR(S) : McKay et al.

It is certified that error appears in the above-identified patent and that said Letters Patent is hereby corrected as shown below:

Column 51,
Line 2, please delete "and meh" and insert therefor -- through --.
Line 20, please delete "othter" and insert therefor -- other --.

Signed and Sealed this

Twenty-second Day of January, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 5,877,309
DATED         : March 2, 1999
INVENTOR(S)   : McKay et al.

It is certified that error appears in the above-identified patent and that said Letters Patent is hereby corrected as shown below:

Column 4,
Line 60, please delete "expressioat" and insert therefor -- expression --.

Column 9,
Line 52, please delete "10:111" and insert therefor -- 10:1111 --.

Column 12,
Line 42, please delete "846" and insert therefor -- (84%) --.

Column 23,
Line 59, please delete "opacities" and insert therefor -- opacifiers --.

Column 34,
Table 4, ISIS No. 15345, please delete
"$C^S T^S C^S T^S C^S T^S G^S T^S A^S G^S G^S C^S C^S C^S G^S C^S T^S T^S G^S G$" and insert therefor --
$C^S T^S C^S T^S C^S T^S G^S T^S A^S G^S G^S C^S C^S C^S G^S C^S T^S T^S G^S G$ --.
Table 4, ISIS No. 15346, please delete
"$C^S T^S C^S T^S C^S T^S G^S T^S A^S G^S G^S C^S C^S C^S G^S C^S T^S T^S G^S G$" and inser therefor --
$C^S T^S C^S T^S C^S T^S G^S T^S A^S G^S G^S C^S C^S C^S G^S C^S T^S T^S G^S G$ --.
Table 4, ISIS No. 15347, please delete
"$C^O T^O C^O T^O C^S T^S G^S T^S A^S G^S G^S C^S C^S C^S G^O C^O T^O T^O G^O G$" and insert therefor --
$C^O T^O C^O T^O C^S T^S G^S T^S A^S G^S G^S C^S C^S C^S G^O C^O T^O T^O G^O G$ --.
Table 4, ISIS No. 15348, please delete
"$C^S T^S C^S T^S C^S T^S G^S T^S A^S G^S G^S C^S C^S C^S G^S C^S T^S T^S G^S G$" and inset therefor --
$C^S T^S C^S T^S C^S T^S G^S T^S A^S G^S G^S C^S C^S C^S G^S C^S T^S T^S G^S G$ --.
Table 4, ISIS No. 15349, please delete
"$C^S T^S C^S T^S C^S T^S G^S T^S A^S G^S G^S C^S C^S C^S G^S C^S T^S T^S G^S G$" and insert therfor --
$C^S T^S C^S T^S C^S T^S G^S T^S A^S G^S G^S C^S C^S C^S G^S C^S T^S T^S G^S G$ --.
Table 4, ISIS No. 15351, please delete
"$C^O T^O C^O T^O C^O T^O G^O T^O A^O G^O G^S C^S C^S C^S G^S C^S T^S T^S G^S G$" an insert therefor --
$C^O T^O C^O T^O C^O T^O G^O T^O A^O G^O G^S C^S C^S C^S G^S C^S T^S T^S G^S G$ --.
Table 4, ISIS No. 15350, please delete
"$C^S T^S C^S T^S C^S T^S G^S T^S A^S G^O G^O C^O C^O C^O G^O C^O T^O T^O G^O G$" and insert therefor --
$C^S T^S C^S T^S C^S T^S G^S T^S A^S G^O G^O C^O C^O C^O G^O C^O T^O T^O G^O G$ --.

Column 35,
Line 2, please delete "C" and insert therefor -- "C" --.

Column 39,
Line 28, in SEQ ID NO. 71, please delete
"5' -CCCTCTCCTTTAGCACAGGTGCAGCAGTGATC"

UNITED STATES PATENT AND TRADEMARK OFFICE
CERTIFICATE OF CORRECTION

PATENT NO.    : 5,877,309
DATED         : March 2, 1999
INVENTOR(S)   : McKay et al.

It is certified that error appears in the above-identified patent and that said Letters Patent is hereby corrected as shown below:

Column 43,
Table 11, ISIS No. 15352, please delete
"$G^S T^S C^S C^S G^S G^S G^S C^S C^S A^S G^S G^S C^S C^S A^S A^S A^S G^S T^S C$" and insert therefor
-- $\mathbf{G^S T^S C^S C^S G^S G^S G^S C^S C^S A^S G^S G^S C^S C^S A^S A^S A^S G^S T^S C}$ --.
Table 11, ISIS No. 15353, please delete
"$G^S T^S C^S C^S G^S G^S G^S C^S C^S A^S G^S G^S C^S C^S A^S A^S A^S G^S T^S C$" and insert therefor
-- $\mathbf{G^S T^S C^S C^S G^S G^S G^S C^S C^S A^S G^S G^S C^S C^S A^S A^S A^S G^S T^S C}$ --.
Table 11, ISIS No. 15354, please delete
"$G^O T^O C^O C^O G^S G^S G^S C^S C^S A^S G^S G^S C^S C^S A^O A^O A^O G^O T^O C$" and insert therefor
-- $\mathbf{G^O T^O C^O C^O G^S G^S G^S C^S C^S A^S G^S G^S C^S C^S A^O A^O A^O G^O T^O C}$ --
Table 11, ISIS No. 15355, please delete
"$G^S T^S C^S C^S G^S G^S G^S C^S C^S A^S G^S G^S C^S C^S A^S A^S A^S G^S T^S C$" and insert therefor
-- $\mathbf{G^S T^S C^S C^S G^S G^S G^S C^S C^S A^S G^S G^S C^S C^S A^S A^S A^S G^S T^S C}$ --.
Table 11, ISIS No. 15356, please delete
"$G^S T^S C^S C^S G^S G^S G^S C^S C^S A^S G^S G^S C^S C^S A^S A^S A^S G^S T^S C$" and insert therefor
-- $G^S T^S C^S C^S G^S G^S G^S C^S C^S \mathbf{A^S G^S G^S C^S C^S A^S A^S A^S G^S T^S C}$ --.
Table 11, ISIS No. 15358, please delete
"$G^O T^O C^O C^O G^O G^O G^O C^O C^O A^O G^S G^S C^S C^S A^S A^S A^S G^S T^S C$" and insert therefore
-- $\mathbf{G^O T^O C^O C^O G^O G^O G^O C^O C^O A^O G^S G^S C^S C^S A^S A^S A^S G^S T^S C}$ --.
Table 11, ISIS No. 15357, please delete
"$G^S T^S C^S C^S G^S G^S G^S C^S C^S A^O G^O G^O C^O C^O A^O A^O A^O G^O T^O C$" and insert therefore
-- $G^S T^S C^S C^S G^S G^S G^S C^S C^S \mathbf{A^O G^O G^O C^O C^O A^O A^O A^O G^O T^O C}$ --.

Column 46,
Seq. ID# 79, please delete
"5' -GATCAGCCTTCAGCACAGATGCAGCAGTAAGTAGC" and insert therefor
-- 5' -GATCAGCCTTCAGCACAGATGCAGCAGTAAGTAGC --.

Column 48,
Table 14, ISIS No. 16690, please delete "TTC-AAC-AGT-TTC-TTG-CAT-AA" and insert therefore -- TTC–AAC–AGT–TTC–TTG–CAT–AA --.
Table 14, ISIS No. 16691, please delete "CTC–ATC–TAT–AGG–AAA–CGG–GT" and insert therefor -- CTC–ATC–TAT–AGG–AAA–CGG–GT --.
Table 14, ISIS No. 16692, please delete "TGG–AGG–CTC–ATA–AAT–ACC–AC" and insert therefore -- TGG–AGG–CTC–ATA–AAT–ACC–AC --.
Table 14, ISIS No. 16693, please delete "TAT–AAG–AAA–TGG–AGG–CTC–AT" and insert therefor -- TAT–AAG–AAA–TGG–AGG–CTC–AT --.
Table 14, ISIS No. 16694, please delete "TCA–CAT–CCA–ATG–TTG–GTT–CA" and insert therefor -- TCA–CAT–CCA–ATG–TTG–GTT–CA --.

UNITED STATES PATENT AND TRADEMARK OFFICE
CERTIFICATE OF CORRECTION

PATENT NO.   : 5,877,309
DATED        : March 2, 1999
INVENTOR(S)  : McKay et al.

It is certified that error appears in the above-identified patent and that said Letters Patent is hereby corrected as shown below:

Column 48, cont'd,
Table 14, ISIS No. 16695, please delete "TTA–TCG–AAT–CCC–TGA–CAA–AA" and insert therefor -- TTA–TCG–AAT–CCC–TGA–CAA–AA --.
Table 14, ISIS No. 16696, please delete "GTT–TGG–CAA–TAT–ATG–ACA–CA" and insert therefor -- GTT–TGG–CAA–TAT–ATG–ACA–CA --.
Table 14, ISIS No. 16697, please delete " CTG–TCA–AGG–ACA–GCA–TCA–TA" and insert therefore -- CTG–TCA–AGG–ACA–GCA–TCA–TA --.
Table 14, ISIS No. 16698, please delete "AAT–CAC–TTG–ACA–TAA–GTT–GG" and insert therefor -- AAT–CAC–TTG–ACA–TAA–GTT–GG --.
Table 14, ISIS No. 16699, please delete "TAA–ATC–CCT–GTG–AAT–AAT–TC" and insert therefor -- TAA–ATC–CCT–GTG–AAT–AAT–TC --.
Table 14 ISIS No. 16700, please delete "GCA–TCC–CAC–AGA–CCA–TAT–AT" and insert therefor -- GCA–TCC–CAC–AGA–CCA–TAT–AT --.
Table 14, ISIS No. 16702, please delete "TGT–TCT–CTT–TCA–TCC–AAC–TG" and insert therefor -- TGT–TCT–CTT–TCA–TCC–AAC–TG --.
Table 14, ISIS No. 16703, please delete "TCT–CAC–TGC–TGT–TCA–CTG–CT" and insert therefor -- TCT–CAC–TGC–TGT–TCA–CTG–CT --.
Table 14, ISIS No. 16704, please delete "GGG–TCT–GGT–CGG–TGG–ACA–TG" and insert therefor -- GGG–TCT–GGT–CGG–TGG–ACA–TG --.
Table 14, ISIS No. 16705, please delete "AGG–CTG–CTG–TCA–GTG–TCA–GA" and insert therefore -- AGG–CTG–CTG–TCA–GTG–TCA–GA --.
Table 14 ISIS No. 16706, please delete "TCA–CCT–GCA–ACA–ACC–CAG–GG" and insert therefor -- TCA–CCT–GCA–ACA–ACC–CAG–GG --.
Table 14, ISIS No. 16707, please delete "GCG–GCT–AGT–CAC–CTG–CAA–CA" and insert therefor -- GCG–GCT–AGT–CAC–CTG–CAA–CA --.
Table 14, ISIS No. 16708, please delete "CGC–TGG–GTT–TCG–CAG–GCA–GG" and insert therefor -- CGC–TGG–GTT–TCG–CAG–GCA–GG --.
Table 14, ISIS No. 16709, please delete "ATC–ATC–TCC–TGA–AGA–ACG–CT" and insert therefor -- ATC–ATC–TCC–TGA–AGA–ACG–CT --.

Column 49,
Line 41, please delete "EMBLO" and insert therefore -- EMBO --.

Column 50,
In SEQ ID 83, please delete "GGACAGCCTTCTCCTTCAGCACAGGTGCAGCAGTGAAC" and insert there for --GGACAGCCTTCTCCTTCAGCACAGGTGCAGCAGTGAAC--. The last TGA needs to be emboldened.

UNITED STATES PATENT AND TRADEMARK OFFICE
CERTIFICATE OF CORRECTION

PATENT NO.    : 5,877,309
DATED         : March 2, 1999
INVENTOR(S)   : McKay et al.

It is certified that error appears in the above-identified patent and that said Letters Patent is hereby corrected as shown below:

<u>Column 51,</u>
Line 2, please delete "and meh" and insert therefor -- through --.
Line 20, please delete "othter" and insert therefor -- other --.

This Certificate supersedes Certificate of Correction issued January 22, 2002.

Signed and Sealed this

Thirteenth Day of August, 2002

*Attest:*

*Attesting Officer*

JAMES E. ROGAN
*Director of the United States Patent and Trademark Office*